US012453856B2

(12) United States Patent
Brown

(10) Patent No.: US 12,453,856 B2
(45) **Date of Patent: *Oct. 28, 2025**

(54) EXTERNAL AUDITORY CANAL THERAPY DEVICE

(71) Applicant: Neuraxis, Inc., Versailles, IN (US)

(72) Inventor: Christopher R. Brown, Greensburg, IN (US)

(73) Assignee: Neuraxis, Inc., Carmel, IN (US)

(*) Notice: Subject to any disclaimer, the term of this patent is extended or adjusted under 35 U.S.C. 154(b) by 460 days.

This patent is subject to a terminal disclaimer.

(21) Appl. No.: 17/861,646

(22) Filed: Jul. 11, 2022

(65) Prior Publication Data

US 2022/0347474 A1 Nov. 3, 2022

Related U.S. Application Data

(63) Continuation-in-part of application No. 17/589,082, filed on Jan. 31, 2022, which is a continuation-in-part (Continued)

(51) Int. Cl.

| | |
|---|---|
| ***A61N 1/36*** | (2006.01) |
| ***A61N 1/04*** | (2006.01) |
| ***A61N 5/06*** | (2006.01) |

(52) U.S. Cl.

CPC ....... *A61N 1/36036* (2017.08); *A61N 1/0456* (2013.01); *A61N 5/0603* (2013.01);

(Continued)

(58) Field of Classification Search

CPC .... A61N 2005/0605; A61N 2005/0626; A61N 2005/0647; A61N 2005/0651;

(Continued)

(56) References Cited

U.S. PATENT DOCUMENTS

| | | | |
|---|---|---|---|
| 5,084,007 | A | 1/1992 | Malin |
| 8,308,784 | B2 | 11/2012 | Streeter et al. |

(Continued)

FOREIGN PATENT DOCUMENTS

| | | | |
|---|---|---|---|
| CN | 105879224 A | * | 8/2016 |
| JP | 2014505509 A | | 3/2014 |

(Continued)

OTHER PUBLICATIONS

PCT International Search Report and Written Opinion completed by the ISA/US on Aug. 26, 2020 and issued in connection with PCT/US2020/039040.

(Continued)

*Primary Examiner* — Shirley X Jian
*Assistant Examiner* — Vynn V Huh
(74) *Attorney, Agent, or Firm* — Barnes & Thornburg LLP

(57) ABSTRACT

An external auditory canal therapy device may include a housing inserted into an external auditory canal of a human ear, at least one electrically conductive electrode coupled to the housing and one or both of at least one irradiation source and at least one speaker coupled to the housing. An electrical circuit carried by the housing may control the at least one electrically conductive electrode to provide electrically stimulation through the dermis to at least one of an arterial branch and a peripheral nerve branch of at least one cranial nerve, and may control one or both of the at least one irradiation source to irradiate the at least one of the arterial branch and the peripheral nerve branch of the at least one cranial nerve through the dermis and the at least one speaker to produce acoustic waves directed toward a tympanic membrane of the ear.

20 Claims, 14 Drawing Sheets

Related U.S. Application Data of application No. 17/617,364, filed as application No. PCT/US2020/039040 on Jun. 23, 2020.

(60) Provisional application No. 62/866,763, filed on Jun. 26, 2019.

(52) U.S. Cl.
CPC ................ *A61N 2005/0605* (2013.01); *A61N 2005/0647* (2013.01); *A61N 2005/0662* (2013.01)

(58) Field of Classification Search
CPC .... A61N 2005/0662; A61N 2005/0663; A61N 5/0603; A61N 5/0622; A61N 5/06–2005/073; H04R 1/02; H04R 1/028; H04R 1/1016; H04R 1/1041
USPC .......... 607/1–95, 115–156, 88–94; 606/2–19
See application file for complete search history.

(56) References Cited

U.S. PATENT DOCUMENTS

| | | | | |
|---|---|---|---|---|
| 8,535,361 | B2 | 9/2013 | Lim et al. | |
| 9,258,642 | B2 | 2/2016 | Nissila et al. | |
| 2003/0195588 | A1* | 10/2003 | Fischell | A61N 2/02 607/55 |
| 2008/0146549 | A1 | 6/2008 | Coleman | |
| 2012/0253427 | A1 | 10/2012 | Aunio et al. | |
| 2013/0301851 | A1* | 11/2013 | Nissila | A61N 5/0618 381/74 |
| 2015/0112405 | A1 | 4/2015 | Brown et al. | |
| 2015/0112411 | A1 | 4/2015 | Beckman | |
| 2018/0200522 | A1 | 7/2018 | Taca, Jr. | |
| 2018/0256917 | A9 | 9/2018 | Lim | |
| 2018/0280721 | A1 | 10/2018 | Beckner et al. | |
| 2020/0121544 | A1* | 4/2020 | George | G16H 20/17 |
| 2022/0072311 | A1 | 3/2022 | Taca, Jr. | |

FOREIGN PATENT DOCUMENTS

| | | | |
|---|---|---|---|
| KR | 20140006236 | A | 1/2014 |
| WO | 2015/008154 | A2 | 1/2015 |
| WO | 2016/151377 | A1 | 9/2016 |
| WO | 2017/044967 | A1 | 3/2017 |
| WO | 2019/053625 | A1 | 3/2019 |

OTHER PUBLICATIONS

Vernon Furtado Da Silva, et al.; Stimulation by Light and Sound: Therapeutics Effects in Humans. Systematic Review; Clinical Practice and Epidemiology in Mental Health; Jun. 25, 2015.
Vasileios Gkolias, et al; Reduced pain and analgesic use after acoustic binaural beats therapy in chronic pain—A double-blind randomized control cross-over trial; European Pain Federation; Jul. 27, 2020.
Kim Byung-Hyun, et al; The Effect of White Noise and Pink Noise on the Brain Activity; The Journal of the Korea Contents Association; 2017 (English Google Machine Translation Appended).
Hector D. Orozco Perez, et al; Binaural Beats through the Auditory Pathway: From Brainstem to Connectivity Patterns; National Center for Biotechnology Information eNeuro; Mar. 11, 2020.
Ramaswamy Palaniappan, et al; On the binaural brain entrainment indicating lower heart rate variability; International Journal of Cardiology; Apr. 22, 2015; vol. 190, pp. 262-263.
Patrick A. McConnell, et al; Auditory driving of the autonomic nervous system: Listening to theta-frequency binaural peats post-exercise increases parasympathetic activation and sympathetic withdrawal; Frontiers in Psychology; Nov. 14, 2014.
Michelle T. Graham, et al; Simulations and human cadaver head studies to identify optimal acousiitic receiver locations for minimally invasive photoacoustic-guided neurosurgery; Photoacoustics; May 16, 2020.
John H. Grose, et al; Binaural beat salience; National Center for Biotechnology Information; Feb. 6, 2012.
Leila Chaieb, et al; Auditory beat stimulation and its effects on cognition and mood states; Frontiers in Psychiatry; May 12, 2015.
Miguel Garcia-Argibay, et al; Efficacy of binaural auditory beats in cognition, anxiety, and pain perception: a meta-analysis; Psychological Research; Aug. 2, 2018.
Vera Abeln, et al; Brainwave entrainment for better sleep and post-sleep state of young elite soccer players—A pilot study; European Journal of Sport Science, 2014; vol. 14, No. 5, 393-402.
Qun Wei et al; Novel design of smart sleep-lighting system for improving the sleep environment of children; Technology and Health Care; Jun. 18, 2019; 27(suppl 1); 3-13.
Chandran V. Seshagiri et al; Response Properties of Neighboring Neurons in the Auditory Midbrain for Pure-Tone Stimulation: A Tetrode Study; J Neurophysiol 98: 2058-2073, 2007.
R. Padmanabhan, et al; A prospective, randomised, controlled study examining binaural beat audio and pre-operative anxiety in patients undergoing general anaesthesia for day case surgery; Anaesthesia; Jul. 7, 2005; vol. 60, Issue 9; p. 874-877.
Miranda, Adrian, and Arturo Taca. "Neuromodulation with percutaneous electrical nerve field stimulation is associated with reduction in signs and symptoms of opioid withdrawal: a multisite, retrospective assessment." The American journal of drug and alcohol abuse vol. 44,1 (2018): 56-63. doi:10.1080/00952990.2017.1295459.
Roberts, Arthur and Christopher R. Brown. "Percutaneous Peri-Auricular Peripheral Nerve Field Stimulation: A Novel, Non-Opioid Therapy for Diabetic Neuropathy." The Pain Practitioner, vol. 25, 3 (2015): 41-47.
Non-Final Office Action issued by the USPTO on Sep. 24, 2024, for U.S. Appl. No. 17/617,364 (38 pages).
Response to Non-Final Office Action filed with the USPTO on Dec. 4, 2024, for U.S. Appl. No. 17/617,364 (14 pages).
Final Office Action issued by the USPTO on Mar. 25, 2025, for U.S. Appl. No. 17/617,364 (22 pages).
Response to Final Office Action filed with the USPTO on May 13, 2025, for U.S. Appl. No. 17/617,364 (15 pages).
Advisory Action issued by the USPTO on Jun. 24, 2025, for U.S. Appl. No. 17/617,364 (6 pages).
Response to Advisory Action and Request for Continued Examination filed with the USPTO on Jun. 25, 2025, for U.S. Appl. No. 17/617,364 (13 pages).
Non-Final Office Action issued by the USPTO on Sep. 11, 2024, for U.S. Appl. No. 17/589,082 (33 pages).
Response to Non-Final Office Action filed with the USPTO on Dec. 2, 2024, for U.S. Appl. No. 17/589,082 (14 pages).
Final Office Action issued by the USPTO on Mar. 25, 2025, for U.S. Appl. No. 17/589,082 (21 pages).
Response to Final Office Action and Request for Continued Examination filed with the USPTO on Jun. 25, 2025, for U.S. Appl. No. 17/589,082 (14 pages).

* cited by examiner

EXTERNAL AUDITORY CANAL THERAPY DEVICE

CROSS-REFERENCE TO RELATED APPLICATION

This is a continuation-in-part of U.S. patent application Ser. No. 17/589,082, filed Jan. 31, 2022, which is a continuation-in-part of U.S. patent application Ser. No. 17/617,364, filed Dec. 8, 2021, which is a U.S. national stage entry of International Application Ser. No. PCT/US2020/039040, filed Jun. 23, 2020, which claims the benefit of and priority to Provisional Patent Application No. 62/866,763, filed Jun. 26, 2019, the disclosures of which are all expressly incorporated herein by reference in their entireties.

TECHNICAL FIELD

The present disclosure relates generally to therapy devices including an electrical stimulation feature and at least one of a photobiomodulation feature and a sound therapy feature, and more specifically to devices configured to be inserted into the external auditory canal (also known as the external auditory meatus) of at least one ear of a human or animal and configured to deliver electrical stimulation therapy and at one of photobiomodulation therapy and sound therapy to the human or animal.

BACKGROUND

Pulsed Near-Infrared Photobiomodulation (PNIP) is a technique which uses radiant light energy to modify biological systems with a resulting therapeutic effect. PNIP is known to affect the cranial arteries, nerves, cranial perfusion pressure, and modulate neural oscillations when delivered both transcranially and intra-nasally. Pulsed, rather than steady or static radiation, is believed to reduce the potential over-heating of the adjacent tissues.

Chromophores contain both heme and copper centers which absorb light in the infra-red and near infra-red regions. It is hypothesized that photons disassociate inhibitory nitric oxide leading to an increase in electron transport, mitochondrial membrane potential, ATP production and concurrently activate light-sensitive ion channels allowing calcium to enter the cell after initial photon absorption activates signaling pathways. This acts as a vasodilator and increases lymphatic flow. As a result, the above-noted initial beneficial therapeutic effects of PNIP may be a result of increases in cerebral blood flow (CBF), oxygen consumption, oxygen availability, and increased ATP activity in the mitochondria. While vasodilation reverses shortly after the light stimulation is removed, the changes following exposure to light are known to last for days, weeks, or even months. The long-lasting effects cannot be explained simply by the activation of the mitochondria or stimulation of blood flow alone and is postulated to be as a result of activation of signaling pathways and transcription factors that change protein expression.

Transdermal electrical nerve stimulation (TENS) therapy is another technique which uses electrical stimulation to treat pain and/or other conditions. Audio therapy is yet another technique which uses audio content to provide myriad benefits including, but not limited to, stimulation of brain activity, treatment of pain, treatment of anxiety or the like.

SUMMARY

The present disclosure may comprise one or more of the features recited in the attached claims, and/or one or more of the following features and combinations thereof. In a first aspect, an external auditory canal therapy device may comprise a housing configured to be inserted into an external auditory canal of a human ear, at least one electrically conductive electrode coupled to the housing such that, with the housing inserted into the external auditory canal, at least a portion of the at least one electrically conductive electrode non-percutaneously contacts at least a portion of dermis of the external auditory canal beneath which at least one of an arterial branch and a peripheral nerve branch of at least one cranial nerve is located, at least one of (a) at least one irradiation source coupled to the housing such that, with the housing inserted into the external auditory canal, at least a portion of a radiation emitting surface of the at least one irradiation source faces at least another portion of dermis of the external auditory canal beneath which the at least one of the arterial branch and the peripheral nerve branch of the at least one cranial nerve is located, and (b) at least one speaker carried by the housing such that, with the housing inserted into the external auditory canal, acoustic waves exiting the at least one speaker pass through at least one opening defined through the housing and move through the external auditory canal toward a tympanic membrane of the human ear, and an electrical circuit carried by the housing, the electrical circuit including at least a first circuit component configured to control the at least one electrically conductive electrode to electrically stimulate the at least one of the arterial branch and the peripheral nerve branch of the at least one cranial nerve through the at least a portion of dermis of the external auditory canal, and at least a second circuit component configured to control the at least one of (i) the at least one irradiation source to irradiate the at least one of the arterial branch and the peripheral nerve branch of the at least one cranial nerve through the at least another portion of dermis of the external auditory canal, and (ii) the at least one speaker to produce acoustic waves.

A second aspect may include the features of the first aspect, and wherein the housing has a first portion and a second portion, the first portion of the housing coupled to or integral with the second portion of the housing, the first portion of the housing configured to be inserted into the external auditory canal of the ear, the at least one electrically conductive electrode and the least one of (a) the at least one irradiation source and (b) the at least one speaker coupled to the first portion of the housing, the second portion of the housing containing the electrical circuit.

In a third aspect, an external auditory canal therapy system may include the external auditory canal therapy device having the features of the first aspect and a wireless communication circuit or a communication circuit for conducting hard-wire communications, and may further comprise a mobile communication device including wireless communication circuitry configured to communicate wirelessly with the wireless communication circuit of the external auditory canal therapy device or including communication circuitry configured to communicate with the communication circuit of the external auditory canal therapy device via a hard-wire connection therebetween, the mobile communication device further comprising a processor programmed to control operation of the at least one electrically conductive electrode and operation of the at least one of the at least one irradiation source and the at least one speaker of the external auditory canal therapy device by communicating operating instructions to the electrical circuitry of the external auditory canal therapy device wirelessly or via hard-wire connection.

In a fourth aspect, an external auditory canal therapy apparatus may comprise two of the external auditory canal therapy devices having the features of the first aspect, and wherein the housing of one of the external auditory canal therapy devices is to be inserted into the external auditory canal of one ear of a human and the housing of the other of the external auditory canal therapy devices is to be inserted into the external auditory canal of an opposite ear of the human.

In a fifth aspect, an external auditory canal therapy system may include the two external auditory canal therapy devices of the fourth aspect, wherein the electrical circuitry of each of the two external auditory canal therapy devices includes a wireless communication circuit or a communication circuit for conducting hard-wire communications, and may further comprise a mobile communication device including wireless communication circuitry configured to communicate wirelessly with the wireless communication circuit of each of the two external auditory canal therapy devices or including communication circuitry configured to communicate with the communication circuit of each of the two external auditory canal therapy devices via a hard-wire connection therebetween, the mobile communication device further comprising a processor programmed to control operation of the at least one electrically conductive electrode and the at least one of the at least one irradiation source and the at least one speaker of each of the two external auditory canal therapy devices by communicating operating instructions to the electrical circuitry of each of the two external auditory canal therapy devices wirelessly or via hard-wire connection.

In a sixth aspect, an external auditory canal therapy device may comprise a housing configured to be inserted into an external auditory canal of a human ear, at least one irradiation source coupled to the housing such that, with the housing inserted into the external auditory canal, at least a portion of a radiation emitting surface thereof faces at least a portion of dermis of the external auditory canal beneath which at least one of an arterial branch and a peripheral nerve branch of at least one cranial nerve is located, at least one electrically conductive electrode coupled to the housing such that, with the housing inserted into the external auditory canal, at least a portion of the at least one electrically conductive electrode non-percutaneously contacts at least another portion of dermis of the external auditory canal beneath which at least one of the arterial branch and the peripheral nerve branch of the at least one cranial nerve is located, and an electrical circuit carried by the housing and electrically connected to the at least one irradiation source and to the at least one electrically conductive electrode, the electrical circuit including at least a first circuit component configured to control the at least one irradiation source to irradiate the at least one of the arterial branch and the peripheral nerve branch of the at least one cranial nerve through the at least a portion of dermis of the external auditory canal, and at least a second circuit component configured to control the at least one electrically conductive electrode to electrically stimulate the at least one of the arterial branch and the peripheral nerve branch of the at least one cranial nerve through the at least another portion of dermis of the external auditory canal.

A seventh aspect may include the features of the sixth aspect, and may further comprise means for controlling the at least the first circuit component and the at least the second circuit components to alternatingly cause the at least one irradiation source to produce radiation while the at least one electrically conductive electrode is not electrically stimulating the at least one of the arterial branch and the peripheral nerve branch of the at least one cranial nerve through the at least another portion of dermis of the external auditory canal, and to cause the at least one electrically conductive electrode to electrically stimulate the at least one of the arterial branch and the peripheral nerve branch of the at least one cranial nerve through the at least another portion of dermis of the external auditory canal while the at least one irradiation source is not producing radiation.

An eighth aspect may include the features of the sixth aspect, and may further comprise means for controlling the at least the first circuit component and the at least the second circuit components to simultaneously cause the at least one irradiation source to produce radiation and the at least one electrically conductive electrode to electrically stimulate the at least one of the arterial branch and the peripheral nerve branch of the at least one cranial nerve through the at least another portion of dermis of the external auditory canal.

A ninth aspect may include the features of the sixth aspect, and wherein the at least one irradiation source is configured to produce electromagnetic radiation in at least one frequency or range of frequencies of visible light.

A tenth aspect may include the features of the sixth aspect, wherein at least a portion of the housing has a curved outer periphery, and wherein the at least one irradiation source and the at least one electrically conductive electrode include two or more irradiation sources and two or more electrically conductive electrodes disposed radially about the curved outer periphery.

In an eleventh aspect, an external auditory canal therapy system, may comprise the external auditory canal therapy device having the features of the sixth aspect, wherein the electrical circuitry of the external auditory canal therapy device includes a wireless communication circuit or a communication circuit for conducting hard-wire communications, and may further comprise a mobile communication device including wireless communication circuitry configured to communicate wirelessly with the wireless communication circuit of the external auditory canal therapy device or including communication circuitry configured to communicate with the communication circuit of the external auditory canal therapy device via a hard-wire connection therebetween, the mobile communication device further comprising a processor programmed to control operation of the at least one irradiation source and the at least one electrically conductive electrode of the external auditory canal therapy device by communicating operating instructions to the electrical circuitry of the external auditory canal therapy device wirelessly or via hard-wire connection.

In a twelfth aspect, an external auditory canal therapy apparatus may comprise two external auditory canal therapy devices each having the features of the sixth aspect, wherein the housing of one of the external auditory canal therapy devices is to be inserted into the external auditory canal of one ear of a human and the housing of the other of the external auditory canal therapy devices is to be inserted into the external auditory canal of an opposite ear of the human.

In a thirteenth aspect, an external auditory canal therapy device may comprise a housing configured to be inserted into an external auditory canal of a human ear, the housing defining at least one opening, at least one electrically conductive electrode coupled to the housing such that, with the housing inserted into the external auditory canal, at least a portion of the at least one electrically conductive electrode non-percutaneously contacts at least a portion of dermis of the external auditory canal beneath which at least one of an arterial branch and a peripheral nerve branch of at least one cranial nerve is located, at least one speaker carried by the housing such that, with the housing inserted into the external auditory canal, acoustic waves exiting the at least one speaker pass through the at least one opening of the housing and move through the external auditory canal toward a tympanic membrane of the ear, and an electrical circuit carried by the housing and electrically connected to the at least one electrically conductive electrode and to the at least one speaker, the electrical circuit including at least a first circuit component configured control the at least one electrically conductive electrode to electrically stimulate the at least one of the arterial branch and the peripheral nerve branch of the at least one cranial nerve through the at least a portion of dermis of the external auditory canal, and at least a second circuit component configured to control the at least one speaker to produce acoustic waves.

A fourteenth aspect may include the features of the thirteenth aspect, and may further comprise means for controlling the at least the first circuit component and the at least the second circuit components to alternatingly cause the at least one irradiation source to electrically stimulate the at least one of the arterial branch and the peripheral nerve branch of the at least one cranial nerve through the at least a portion of dermis of the external auditory canal while the at least one speaker is not producing acoustic waves, and to cause the at least one speaker to produce acoustic waves while the at least one irradiation source is not electrically stimulating the at least one of the arterial branch and the peripheral nerve branch of the at least one cranial nerve through the at least a portion of dermis of the external auditory canal.

A fifteenth aspect may include the features of the thirteenth aspect, and may further comprise means for controlling the at least the first circuit component and the at least the second circuit components to simultaneously cause the at least one irradiation source to electrically stimulate the at least one of the arterial branch and the peripheral nerve branch of the at least one cranial nerve through the at least a portion of dermis of the external auditory canal and the at least one speaker to produce acoustic waves.

A sixteenth aspect may include the features of the thirteenth aspect, and wherein the acoustic waves include at least one of single frequency tone signals, multiple frequency tone signals, music signals, noise signals and beat signals.

In a seventeenth aspect, an external auditory canal therapy system, may comprise the external auditory canal therapy device having the features of the thirteenth aspect, wherein the electrical circuitry of the external auditory canal therapy device includes a wireless communication circuit or a communication circuit for conducting hard-wire communications, and may further comprise a mobile communication device including wireless communication circuitry configured to communicate wirelessly with the wireless communication circuit of the external auditory canal therapy device or including communication circuitry configured to communicate with the communication circuit of the external auditory canal therapy device via a hard-wire connection therebetween, the mobile communication device further comprising a processor programmed to control operation of the at least one electrically conductive electrode and the at least one speaker of the external auditory canal therapy device by communicating operating instructions to the electrical circuitry of the external auditory canal therapy device wirelessly or via hard-wire connection.

An eighteenth aspect may include the features of the seventeenth aspect, wherein the mobile communication device has stored therein, or is configured to access externally, one or more audio signal files, and wherein the operating instructions communicated to the external auditory canal therapy device by the mobile communication device include at least one of the one or more audio signal files, and wherein the at least a second control circuit is configured to supply audio signals from the at least one of the one or more audio signal files to the at least one speaker to cause the at least one speaker to produce the acoustic waves in the form of at least one of single frequency tone signals, multiple frequency tone signals, music signals, noise signals and beat signals.

In a nineteenth aspect, an external auditory canal therapy apparatus may comprise two external auditory canal therapy devices each having the features of the thirteenth aspect, wherein the housing of one of the external auditory canal therapy devices is to be inserted into the external auditory canal of one ear of a human and the housing of the other of the external auditory canal therapy devices is to be inserted into the external auditory canal of an opposite ear of the human.

In a twentieth aspect, an external auditory canal therapy device may comprise a housing configured to be inserted into an external auditory canal of a human ear, at least one irradiation source coupled to the housing such that, with the housing inserted into the external auditory canal, at least a portion of a radiation emitting surface thereof faces at least a portion of dermis of the external auditory canal beneath which at least one of an arterial branch and a peripheral nerve branch of at least one cranial nerve is located, at least one electrically conductive electrode coupled to the housing such that, with the housing inserted into the external auditory canal, at least a portion of the at least one electrically conductive electrode non-percutaneously contacts at least another portion of dermis of the external auditory canal beneath which at least one of the arterial branch and the peripheral nerve branch of the at least one cranial nerve is located, at least one speaker carried by the housing such that, with the housing inserted into the external auditory canal, acoustic waves exiting the at least one speaker pass through at least one opening of the housing and move through the external auditory canal toward a tympanic membrane of the ear, and an electrical circuit carried by the housing and electrically connected to the at least one irradiation source, the at least one electrically conductive electrode and the at least one speaker, the electrical circuit including at least a first circuit component configured to control the at least one irradiation source to irradiate the at least one of the arterial branch and the peripheral nerve branch of the at least one cranial nerve through the at least a portion of dermis of the external auditory canal, at least a second circuit component configured to control the at least one electrically conductive electrode to electrically stimulate the at least one of the arterial branch and the peripheral nerve branch of the at least one cranial nerve through the at least another portion of dermis of the external auditory canal, and at least a third circuit component configured to control the at least one speaker to produce acoustic waves.

DESCRIPTION OF THE ILLUSTRATIVE EMBODIMENTS

For the purposes of promoting an understanding of the principles of this disclosure, reference will now be made to a number of illustrative embodiments shown in the attached drawings and specific language will be used to describe the same.

Figure 1A:
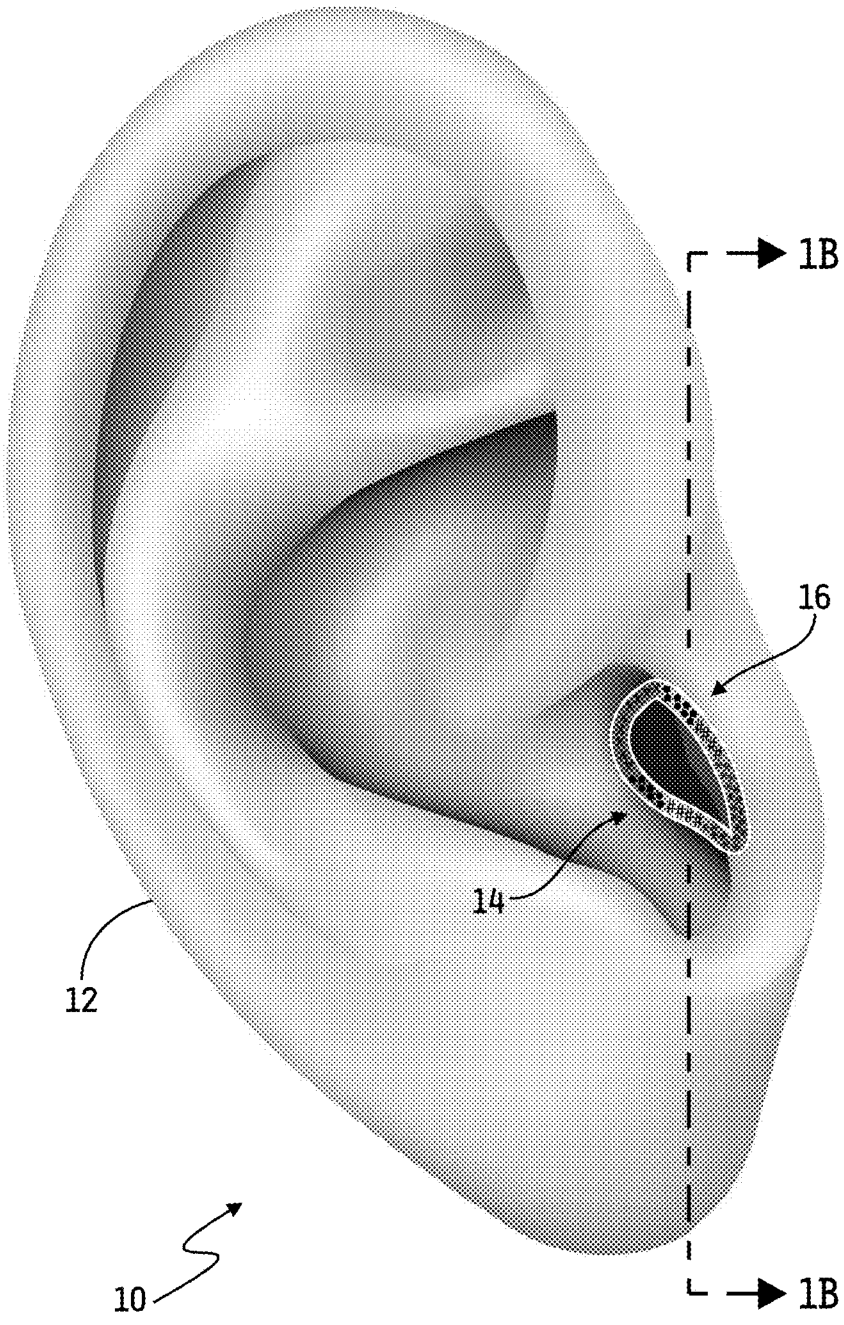
FIG. 1A is a perspective view of a human ear illustrating auricular innervation in and about an external entrance of the external auditory meatus.
Figure 1B:
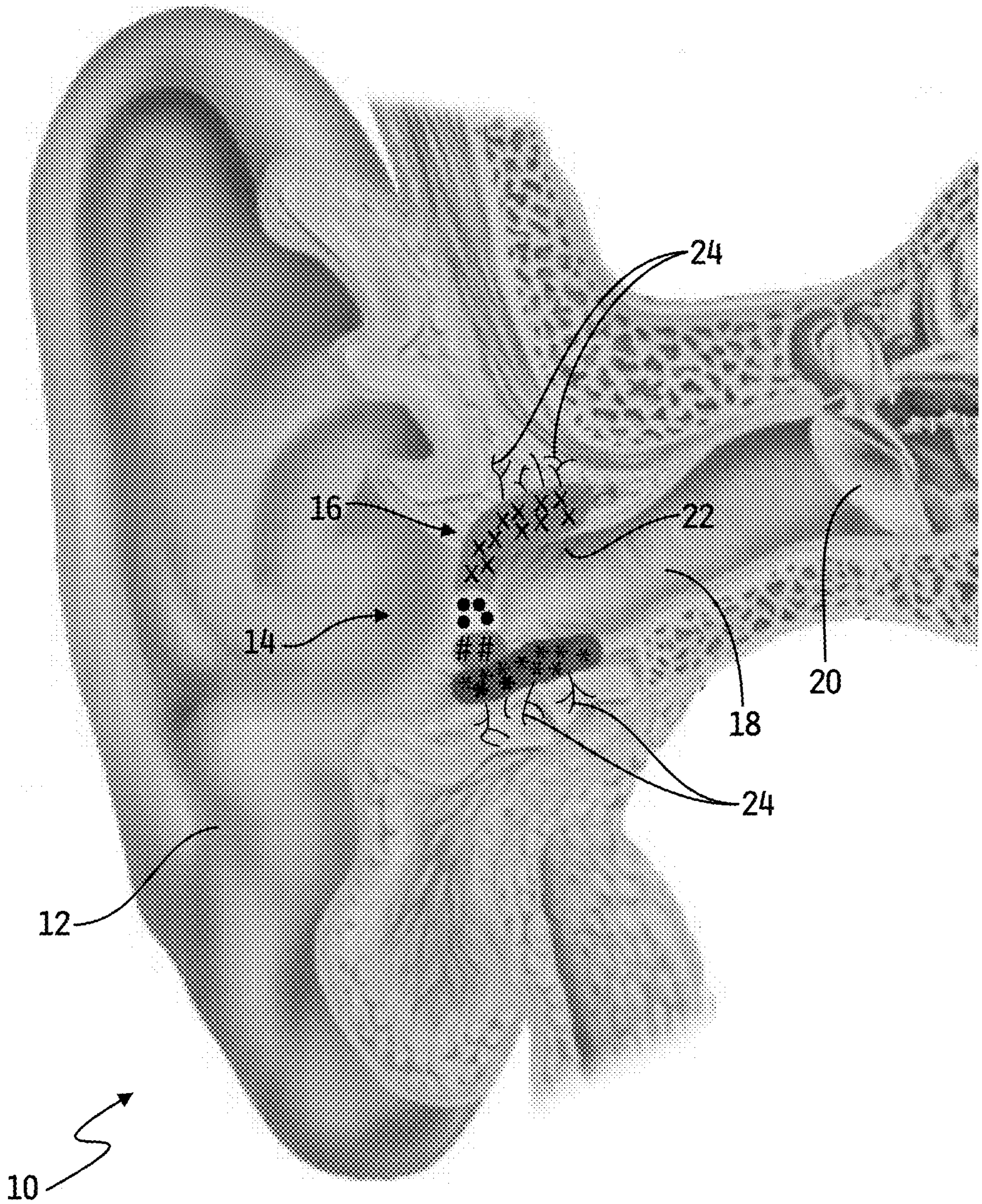
FIG. 1B is a partial cross-sectional view of the human ear of FIG. 1A as viewed along section lines 1B-1B thereof, illustrating distribution of cranial nerves V (*), VII (#), IX (●) and X (X) and arterial branches about the external entrance of the external auditory meatus and extending at least partially into the external auditory meatus.

This disclosure relates to devices and techniques for irradiating at least a portion of the external auditory meatus of a human or animal ear for the purpose of stimulating a peripheral branch of at least one cranial nerve and/or stimulating at least one arterial branch anatomically located beneath the dermis in the external auditory meatus. Referring to FIGS. 1A and 1B, for example, a human ear 10 is shown depicting the auricle 12 and an entrance opening 14 to the external auditory meatus 18 defined and extending between the entrance opening 14 and the tympanic membrane 20. As illustrated by example in FIGS. 1A and 1B, peripheral branches of a number of cranial nerves 16 extend about the periphery of the entrance opening 14 and at least partially into the external auditory meatus 18 beneath the dermis 22. In particular, a peripheral branch of the trigeminal nerve (sometimes referred to as "V"), depicted in FIGS. 1A and 1B as "*," extends along an arcuate anterior portion of the entrance opening 14 and at least partially into the external auditory meatus 18. Likewise, a peripheral branch of the vagus nerve (sometimes referred to as "X"), depicted in FIGS. 1A and 1B as "X," extends along an arcuate posterior portion of the entrance opening 14 and at least partially into the external auditory meatus 18. Top and bottom peripheral branches of the facial nerve (sometimes referred to as "VII"), depicted in FIGS. 1A and 1B as "#," extend along top and bottom portions of the entrance opening 14 next to opposite arcuate ends of the trigeminal nerve V (*), and top and bottom peripheral branches of the glossopharangeal nerve (sometimes referred to as "IX"), depicted in FIGS. 1A and 1B as "●," extend along top and bottom portions of the entrance opening 14 next to opposite arcuate ends of the vagus nerve X (X) and next to respective top and bottom peripheral branches of the facial nerve VII (#). As illustrated by example in FIG. 1B, the facial nerve branches VII (#) and the glossopharangeal nerve branches IX (●) both extend at least partially into the external auditory meatus 18 from the entrance opening 14, although the trigeminal nerve branch V (*) and the vagus nerve branch X (X) each extend substantially further into the external auditory meatus 18 by comparison. Arterial branches 24 are also illustrated in FIG. 1B extending at least partially about the external auditory meatus 18 in and/or adjacent to the region containing the cranial nerves 16.

Figure 2A:
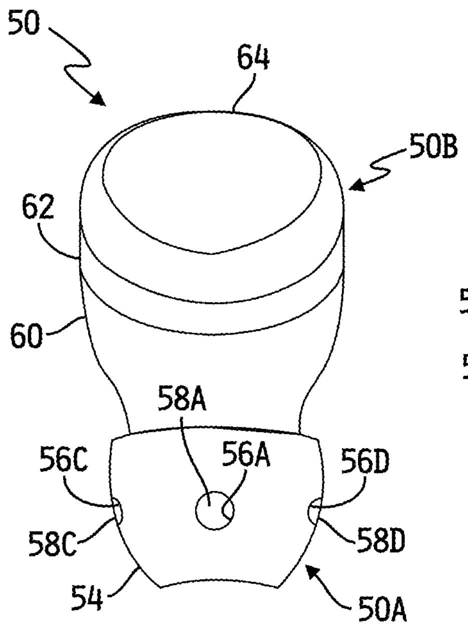
FIG. 2 includes FIGS. 2A-2D which illustrate various views of an embodiment of an external auditory canal photobiomodulation device.
Figure 2B:
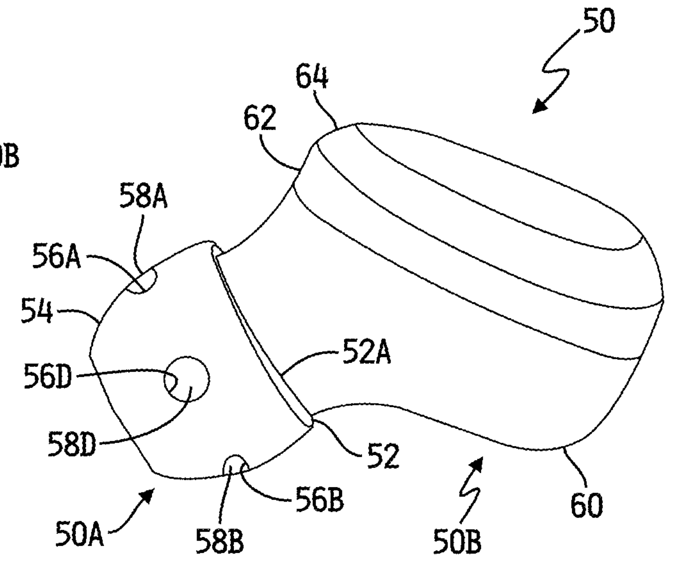
Figure 2C:
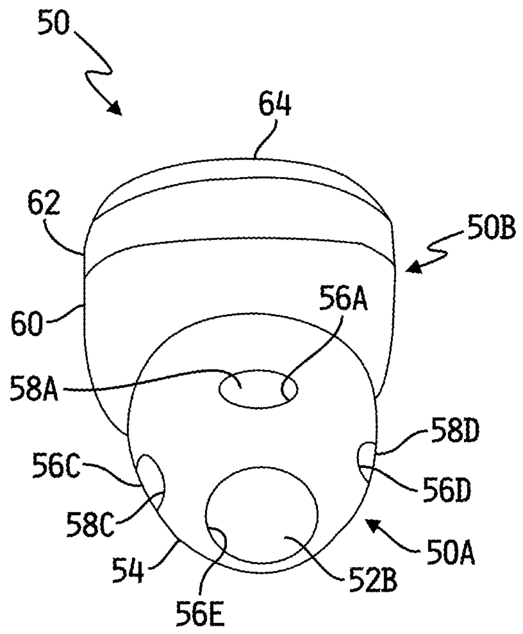
Figure 2D:
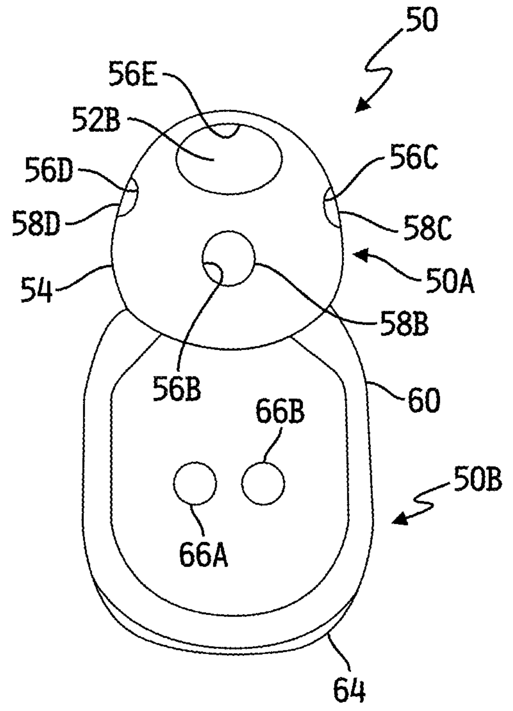
Figure 3:
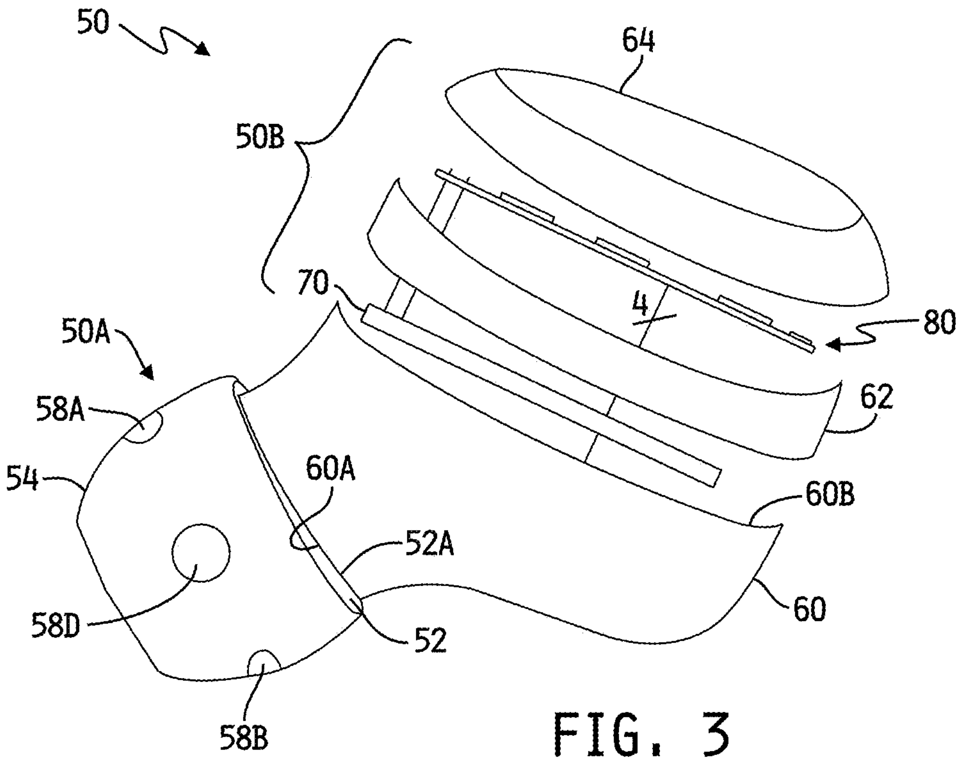
FIG. 3 is a partial assembly view of the external auditory canal photobiomodulation device of FIGS. 2A-2D showing placement of a power source and control circuitry within a housing of the device.
Figure 4:
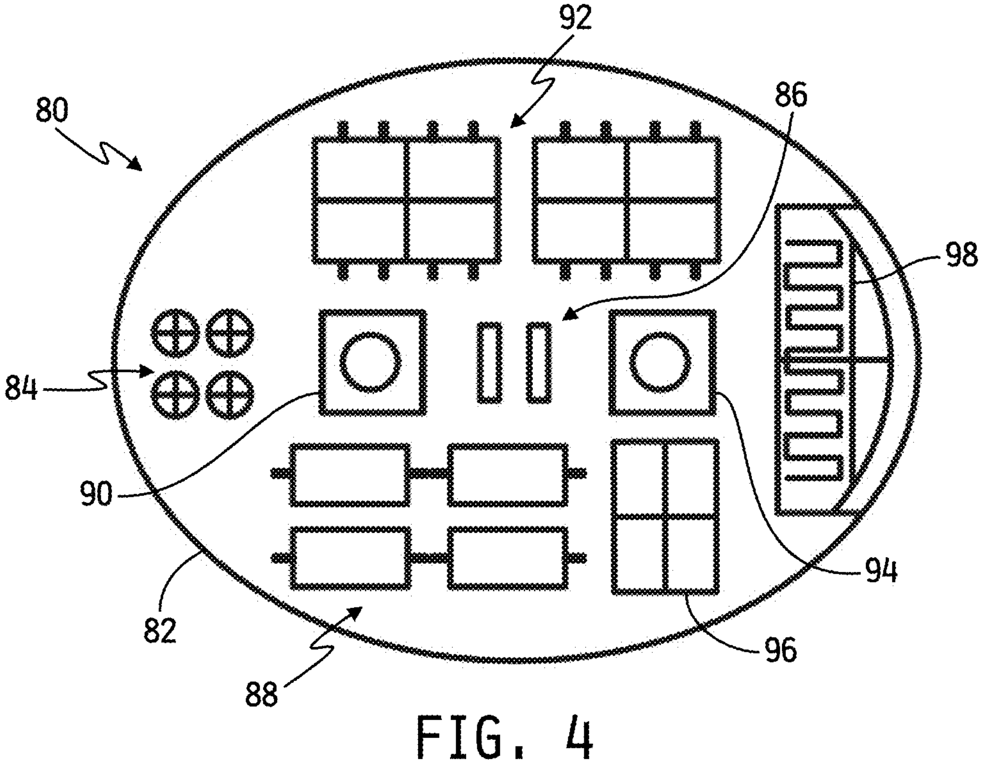
FIG. 4 is a top plan view of an embodiment of the control circuitry of the external auditory canal photobiomodulation device illustrated in FIG. 3.

Referring now to FIGS. 2A-2D an embodiment is shown of a photobiomodulation device 50 configured to be placed in transdermal contact with the external auditory meatus 18 of a human ear 10 at the external opening 14 thereto, and to be controlled to irradiate at least one of the peripheral branches of one or more of the cranial nerves 16 and/or of one or more arterial branches 24 extending about the periphery of the entrance opening 14 and at least partially into the external auditory meatus 18 beneath the dermis 22. In some embodiments, only a single such device 50 is implemented, although in other embodiments two such devices 50 are implemented; one inserted into each ear of the user. In the illustrated embodiment, the device 50 includes an external auditory meatus insertion portion 50A implemented in a form similar to a conventional "earbud," and a control portion 50B including a source of electrical power as well as control and wireless communication electronics. Examples of the latter are illustrated in FIGS. 3 and 4 which will be described in detail below.

The external auditory meatus insertion portion 50A illustratively includes a generally curved, e.g., dome-shaped, housing 52 having an open end 52A and a curved outer surface which illustratively tapers downwardly in cross-section toward an opposite end 52B thereof, wherein the housing 52 is generally sized and configured to be received, leading with the end 52B, through the entrance opening 14 and at least partially into the external auditory meatus 18 of a human ear 10. In some embodiments, a flexible ear tip or ear cap 54 is provided, which is generally shaped similarly to the housing 52 and within which the housing 52 is received. In such embodiments, the ear tip or cap 54 may illustratively be formed of silicone or other material(s) configured facilitate frictional transdermal engagement of the ear tip or cap 54 with the tissue lining extending circumferentially about the entrance opening 14 and along the external auditory meatus 18 adjacent thereto. In some alternate embodiments in which other conventional structure(s) is/are provided for releasably attaching or affixing the device 50 to the ear 10, the ear tip or cap 54 may be omitted. In any case, the external auditory meatus insertion portion 50A in such embodiments may be sized to be received into, but not necessarily engage, the entrance opening 14 and at least a portion of the external auditory meatus 18 adjacent thereto. In some such embodiments, the external auditory meatus insertion portion 50A may contact but not frictionally engage the entrance opening 14 and/or at least a portion of the external auditory meatus 18 adjacent thereto, and in other such embodiments the device 50 may be designed such that the external auditory meatus insertion portion 50A is insertable through the opening 14 and at least partially into the external auditory meatus 18 but does not contact the entrance opening 14 and/or the external auditory meatus 18 adjacent thereto.

The housing 52 and ear tip or cap 54 (in embodiments which include the ear tip or cap 54) define a number of openings therethrough each sized to receive therein one of a corresponding number of irradiation sources, such that a radiation emitting surface of each of the number of irradiation sources faces a respective portion of the entrance opening 14 and/or at least a portion of the external auditory meatus 18 adjacent thereto. In alternate embodiments, the housing 52 and ear tip or cap 54 (in embodiments which include the ear tip or cap 54) may not define openings per se in which a respective irradiation source is received, but may instead define locations at or in which a respective irradiation source is mounted. In such embodiments, the housing 52 and/or ear tip or cap 54 may define one or more light transmissive portions or windows through which radiation produced by respective ones of the irradiation source may be focused or otherwise transmitted to the peripheral branches of one or more of the cranial nerves 16 and/or toward one or more of the arterial branches 24. In any case, each of the number of irradiation sources illustratively directs radiation produced thereby toward a respective one or more of the peripheral branches of one or more of the cranial nerves 16 and/or toward a respective one or more arterial branches 24 extending about the periphery of the entrance opening 14 and at least partially into the external auditory meatus 18 beneath the dermis 22.

In the illustrated embodiment, four such openings 56A-56D are spaced, e.g., equidistant from one another, radially about the housing 52 and ear tip or cap 54, and four corresponding irradiation sources 58A-58D, e.g., each in the form of a light emitting diode (LED), are provide with each inserted into a respective one of the openings 56A-56D. In this embodiment, the device 50 is illustratively orientable to position each of the irradiation sources 58A-58D opposite to, and facing, the peripheral branches of a respective at least one of the cranial nerves 16 and/or of a respective at least one of the arterial branches in or adjacent to the region containing the cranial nerves 16. For example, the device 50 is illustratively positionable relative to the external auditory meatus 18 such that the irradiation source 58A is opposite the peripheral branches of the cranial nerves VII (#) and IX (●) at the top of the external auditory meatus 18, the irradiation source 58B is opposite the peripheral branches of the cranial nerves VII (#) and IX (●) at the bottom of the external auditory meatus 18, the irradiation source 58C is opposite the peripheral branches of the cranial nerve V (*) at the anterior portion of the external auditory meatus 18 and the irradiation source 58D is opposite the peripheral branches of the cranial nerve X (X) at the posterior portion of the external auditory meatus 18 (e.g., see FIG. 5). One or more of the irradiation sources 58A-58D so positioned may additionally irradiate one or more arterial branches 24 in or adjacent to the various regions of the external auditory meatus 18 containing the respective cranial nerves 16.

It will be understood that above-described positioning of the device 50 is provided only as an illustrative example, and other positions or orientations of the device 50 relative to the external opening 14 and/or to at least a portion of the external auditory meatus 18 adjacent thereto are intended to fall within the scope of this disclosure. It will also be understood that whereas the embodiment illustrated in FIGS. 2A-2D includes four irradiation sources 58A-58D equally-spaced apart radially about the housing 52, alternate embodiments may include more or fewer such irradiation sources equally or non-equally spaced apart radially or otherwise positioned about the housing 52.

It is believed that auricular arterial branches and nerve bundles absorb radiation in the frequency range of red visible light, and reflect radiation in the blue and green frequency ranges. In one example embodiment, the irradiation sources 58A-58D are thus each configured to produce radiation at a frequency, or in the frequency range, of red visible light. In one particular embodiment, the irradiation sources 58A-58D are each illustratively configured to produce radiation at 630 nm. It will be understood, however, that one or more of the irradiation sources 58A-58D may alternatively be configured to produce radiation at any frequency in the frequency range of red visible light, or alternatively still be configured to produce radiation at any frequency in any range of frequencies visible or otherwise. It will be further understood that while the irradiation sources 58A-58D have been described in one embodiment as being implemented in the form of LEDs, one or more of the irradiation sources 58A-58D may alternatively be provided in the form of one or any combination of other conventional irradiation sources configured to produce radiation at any single frequency or in any range of frequencies.

In the illustrated embodiment, the ear tip or cap 54 illustratively includes an axial opening 56E therethrough, e.g., to promote flexibility of the ear tip or cap 54 and/or facilitate frictional fitting of the external auditory meatus insertion portion 50A to the entrance opening 14 and/or at least an adjacent portion of the external auditory meatus 18 of the ear 10. In some embodiments, as illustrated by example in FIGS. 2C and 2D, the opening 56E exposes the domed end 52B of the housing 52. In alternate embodiments, the housing 52 may include a speaker, e.g., a voice coil, magnet and acoustic chamber or other conventional speaker and/or one or more other acoustic devices, and the opening 56E may expose such a speaker to the external auditory meatus 18. In such embodiments, the device 50 may include suitable electronics configured to reproduce sound via the speaker and/or one or more other acoustic devices, e.g., music, speech and/or other audio content. It will be understood that, in some such embodiments in which the housing 52 includes one or more acoustic devices, any such one or more acoustic devices may be or include any device for amplifying and/or transmitting electromagnetic radiation at any frequency or range of frequencies which can be heard, felt and/or otherwise perceived, consciously and/or unconsciously, by a human or other animal. One non-limiting example of such a frequency range may be 20 Hz-20 kHz, although other non-limiting examples may include one or more frequencies below 20 Hz and/or one or more frequencies above 20 kHz, and may generally include one or more frequencies of vibration, sound, ultrasound and/or infrasound.

The control portion 50B of the device 50 illustratively includes a housing 60 having an open end 60A coupled to the open end 52A of the housing 52 of the external auditory meatus insertion portion 50A, and another open end 60B spaced apart from the end 60A. The housing 60 illustratively includes a circuit board carrier sleeve 62 removably coupled to the open end 60B thereof, and a cover 64 removably coupled to the carrier sleeve 62. The housing 60 defines a cavity therein that is illustratively sized to receive, via the open end 60B, a source 70 of electrical power, as illustrated by example in FIG. 3.

In one embodiment, the source 70 of electrical power is implemented in the form of a conventional battery. In some such embodiments, the battery 70 may be rechargeable, and in such embodiments the housing 60 may define openings on the underside thereof via which battery recharging terminals 66A, 66B may be accessed for charging the battery 70, as illustrated by example in FIG. 2D. In alternate embodiments, the battery 70 may be non-rechargeable. In still other embodiments, the source 70 of electrical power may be implemented in the form of one or more other conventional sources of electrical power 70 other than, or in addition to, a battery. In one specific embodiment in which the source 70 of electrical power is provide in the form of a conventional, rechargeable battery, such a battery 70 may be provided in the form of a 3.7 volt, flat pack, 50 mah (milliampere-hours) Lithium battery, although it will be understood that such a specific implementation is described only by way of example, and that the battery 70 may be configured to produce greater or lesser voltage, greater or lesser energy capacity and/or be formed of other active elements and/or compounds. In some alternate embodiments in which the device 50 is hard-wire connected to an electronic control device, e.g., as illustrated by example in FIG. 7 and as described below, electrical power may be supplied by the electronic control device to the device 50. In some such embodiments, the source 70 of electrical power may be omitted.

Referring again to FIG. 3, an electrical circuit 80 is illustratively mounted to and within the circuit board carrier sleeve 62, and the cover 64 is then mounted to the sleeve 62 such that the housing 60 carries the source 70 of electrical power and the electrical circuit 80. In some embodiments, the housing 52 and the housing 60 are separate components attached, connected or otherwise coupled together as described above. In alternative embodiments, the housings 52, 60 may be merged together into a single, unitary housing. In either case, the housing 52 illustratively represents one housing portion configured to be inserted into the external auditory meatus 18 of the ear 10, and the housing 60 represents another housing portion configured to carry the source 70 of electrical power and the electrical circuitry 80.

Referring now to FIG. 4, an embodiment of the electrical circuit 80 is shown. In the illustrated embodiment, the electrical circuit 80 includes a circuit board 82 having a number of different circuit components mounted thereto. The circuit board 82 may illustratively be a conventional rigid, semi-flexible or flexible circuit board configured for surface-mounting and/or through-hole mounting of circuit components thereto. For example, the circuit board 82 illustratively includes electrical terminals or pads 84 configured for connection of electrical power leads or wires thereto. In the embodiment illustrated in FIG. 3, for example, positive (+) and negative (or ground) (−) terminals of the source 70 of electrical power are connected to suitable wires which extend through the circuit board carrier sleeve 62 and into electrical connection with the terminals or pads 84. The circuit board 86 further includes irradiation source terminals 86 or pads configured for connection of irradiation source leads or wires thereto. In the embodiment illustrated in FIG. 3, for example, each of four wires connected to a different respective one of the irradiation sources 58A-58D extends through the open end 52A of the housing 52 of the external auditory meatus insertion portion 50A and into the open end 60A of the housing 60, and then through the circuit board carrier sleeve 62 and into electrical connection with the terminals or pads 86.

Four resistors 88 are mounted to the circuit board 82, and each is electrically coupled at one end through a normally-off switch 90 to the electrical power terminals 84, and each is electrically connected at an opposite end through the terminals or pads 86 to a different respective one of the four irradiation sources 58A-58B. The switch 90 is controllable to an on position, as will be described below, to electrically connect the source 70 of electrical power through the resistors 88 to the irradiation sources 58A-58D to cause the irradiation sources 58A-58D to emit radiation. In one example embodiment in which the source 70 of electrical power is the 3.7 volt battery described above, the irradiation sources 58A-58D are each implemented in the form of a 630 nm, 2 volt, 20 mA, 0.06 Watt LED having a luminance intensity of 240 mcd (milli-candela) and a 120 degree viewing angle, and in this embodiment each of the resistors 88 is implemented in the form of a 60 ohm, 0.25 Watt, +/−1% tolerance, metal film resistor. It will be understood, however, that such an implementation of the irradiation sources 58A-58D and of the resistors 88 is provided only by way of example, and that other irradiation sources 58A-58D and/or other values and/or other specifications of the irradiation sources 58A-58D and/or of the resistors 88 may alternatively be used.

The electrical circuit 80 further illustratively includes a number of integrated circuits 92 mounted to the circuit board 82. In some embodiments, at least one of the integrated circuits 92 is electrically connected to the switch 90 and is configured to control the switch 90 between on and off states at a predefined or programmable switching rate. In one example embodiment, which should not be considered to be limiting in any way, the switching rate is approximately 40 Hz, although other switching rates, or varying switching rates, may alternatively be used. In some such embodiments, the duty cycle of the switching rate is approximately 50%, although in other embodiments the duty cycle may be greater or less than 50%. In some embodiments, one or more of the integrated circuits 92 may control the duty cycle, and in some such embodiments the duty cycle may be programmable or variable. In some embodiments, at least one of the integrated circuits 92 is a conventional driver circuit operatively coupled to the source 70 of electrical power, the switch 90 and/or the resistors 88, and is operable to supply electrical power, and in some embodiments regulate voltage and/or current, from the source 70 of electrical power to the irradiation sources 58A-58D.

The electrical circuit 80 further illustratively includes an on/off switch 94 mounted to the circuit board 82. In some embodiments in which the device 50 is self-controlled, a manually-selectable actuator accessible externally to the housing 60 may be operatively coupled to the switch 94, and the device 50 may be powered on and off via manual actuation of such an actuator. In other embodiments, the device 50 may be hard-wire connected to a remotely located control device, e.g., a mobile or stationary electronic control device, e.g., as illustrated by example in FIG. 7, and in such embodiments the switch 94, and in some cases one or more of the integrated circuits 92, may be electrically connected to the control device, such that the control device hard-wire connected to the device 50 controls operation of the device 50. As described above, in some such embodiments, electrical power may be supplied by the control device to the device 50 through the hard-wire connection, and in such embodiments the power source 70 may (or may not) be omitted from the device 50. Examples of the remotely located control device may include, but are not limited to, a laptop, tablet or personal computer, a mobile communication device such as a mobile phone, smart watch or the like, or other mobile or stationary electronic control device or system.

In still other embodiments, the device 50 is configured to be wirelessly controlled by a wirelessly-connected control device, and in such embodiments wireless communication circuitry may be mounted to the circuit board 82 and electrically connected to at least the switch 94. Such an embodiment is illustrated by example in FIG. 4, in which a wireless communication control circuit 96 is mounted to the circuit board 82 and electrically connected to the switch 94 (either directly or via one or more of the integrated circuits 92), and a wireless communication antenna 98 is also mounted to the circuit board 82 and electrically connected to the wireless communication circuit 96. In one such embodiment, the wireless communication circuit 96 is illustratively implemented in the form of a conventional Bluetooth® controller, and the antenna 98 is a conventional Bluetooth® antenna array, and the Bluetooth® controller 96 is operable in a conventional manner to receive and, in some embodiments, to transmit information in accordance with a conventional Bluetooth® communication protocol. It will be understood, however, that Bluetooth® represents only one example wireless communication protocol that may be implemented in the device 50, and that in alternate embodiments the wireless communication control circuit 96 and antenna 98 may be configured for wireless communication in accordance with one or more other conventional wireless communication protocols.

In embodiments in which the electrical circuit 80 includes wireless communication circuitry as illustrated by example in FIG. 4 and described above, a mobile communication device (MCD) is illustratively provided and programmed to control operation of the photobiomodulation device 50 via instructions communicated wirelessly thereto. Such a programmed MCD may also be used to control operation of the photobiomodulation device 50 in embodiments in which the device 50 is hard-wire connected to the MCD.

Figure 5:
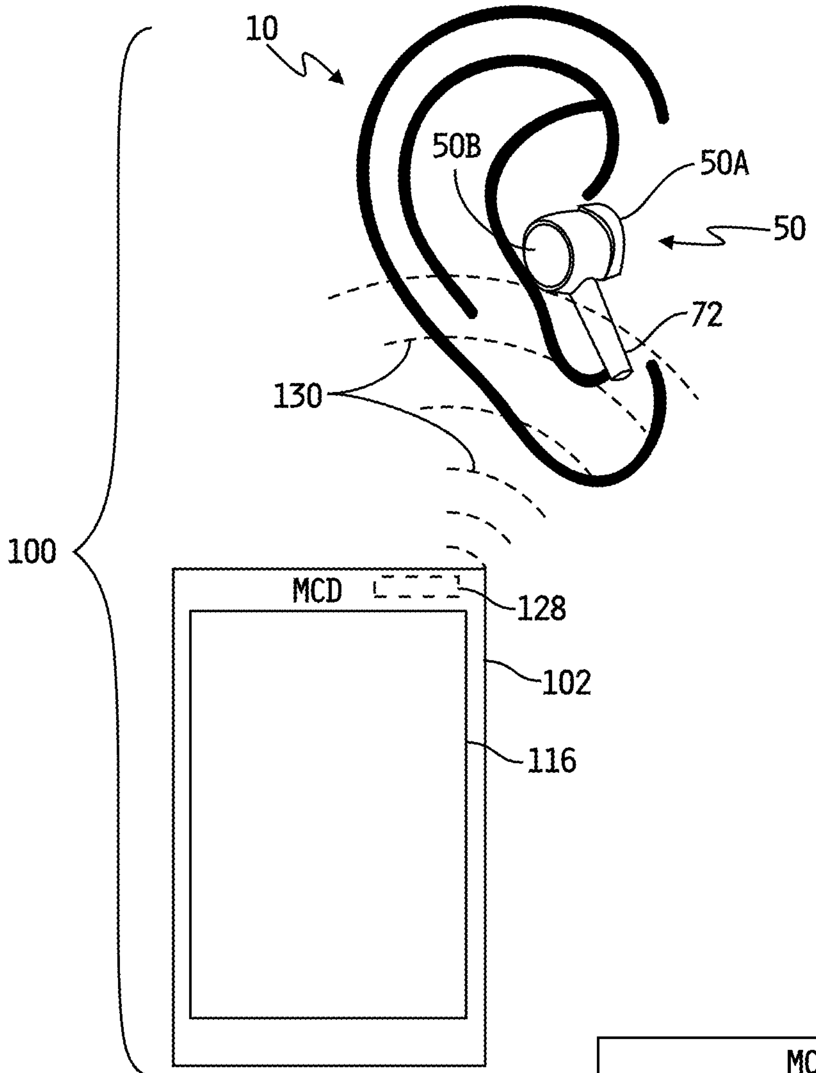
FIG. 5 is a simplified diagram of an embodiment of a photobiomodulation system showing another example of an external auditory canal photobiomodulation device, similar to that illustrated in FIGS. 2A-2D, placed in transdermal contact with the external auditory meatus of a human ear and controlled wirelessly by a software application executed by a mobile communication device.

Referring to FIG. 5, an embodiment is shown of a wirelessly control photobiomodulation system 100 in which a mobile communication device (MCD) 102 with wireless communication capability is configured, i.e., programmed, to control operation of at least one photobiomodulation device 50. In the illustrated embodiment, the external auditory meatus insertion portion 50A of the device 50 illustrated in FIGS. 2A-3 is placed in transdermal contact with the external auditory meatus of a human ear 10 as described above, and the control portion 50B of the device 50 which carries the electrical circuit 80 faces outwardly away from the ear 10 as shown. The MCD 102 is operable to communicate wirelessly with the electrical circuit 80 carried by the device 50 as depicted graphically in FIG. 5 by the wireless communication arcs 130, and is therefore operable to wirelessly control operation of the device 50. In one embodiment, the MCD 102 may be a conventional mobile cell phone, e.g., a so-called smart phone, although in alternate embodiments the MCD 102 may be provided in the form of other conventional or application-specific wireless communication devices. Example of such devices include, but are not limited to, a conventional personal data assistant (PDA), a tablet computer, a key fob, a smart watch, e.g., a standalone device or communicatively coupled to a mobile cell phone, a conventional wireless remote control device, or the like. In the embodiment illustrated in FIG. 5, the device 50 illustratively differs from that illustrated in FIGS. 2A-3 in that the device 50 illustrated in FIG. 5 includes a conventional stem 72 extending generally downwardly from the control portion 50B. The stem 72 may, in some embodiments, be open-ended, and in other embodiments the free end of the stem 72 may be closed, e.g., capped. In some embodiments which include the stem 72, the antenna 98, shown in FIG. 4 as being mounted to the circuit board 82, may extend at least partially into the stem 72. Alternatively or additionally, the stem 72 may house one or more conventional electronic components, examples of which may include, but are not limited to, one or more microphones, one or more force sensors, one or more batteries and/or other sources of electrical power, or other electrical and/or electromechanical devices.

Figure 6:
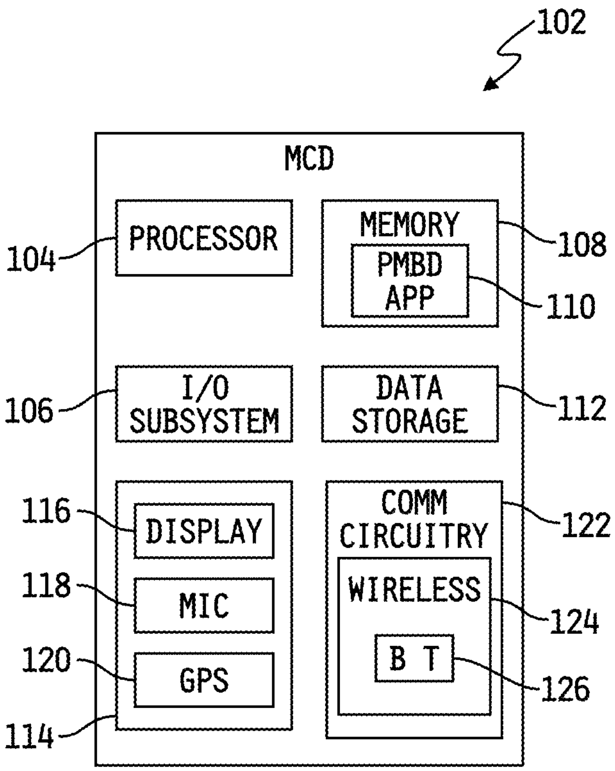
FIG. 6 is a simplified schematic block diagram of the mobile communication device of FIG. 5.

Referring now to FIG. 6, an embodiment of the MCD 102 is shown which illustratively includes a conventional processor 104 operatively coupled to an I/O subsystem 106 which is, in turn, coupled to a memory 108, a data storage 112, a number of peripheral devices 114 and communication circuitry 122. The memory 108 illustratively has stored therein a photobiomodulation device (PBMD) application 110 in the form of instructions executable by the processor 104 to control operation of the photobiomodulation device 50. The data storage 112 is illustratively implemented in the form of one or more conventional memory devices in which data relating to the user of the MCD 102 and/or data relating to operation of the device 50 is stored.

The peripheral devices 114 may include any conventional peripheral devices typically included on a mobile communication device 102 of the type just described. Examples include, but are not limited to, a conventional display screen 116, e.g., touch-controlled or otherwise, a conventional microphone 118 and a conventional GPS module (e.g., including a conventional GPS receiver and associated antenna). Those skilled in the art will recognize other conventional devices that may be included in the peripheral devices 114, and it will be understood that any such other conventional devices are intended to be included within the scope of this disclosure.

The communication circuitry 122 illustratively includes wireless communication circuitry 124, and the wireless communication circuitry 124 may illustratively include any number of wireless communication modules each configured to carry out wireless communications according to a particular communications protocol. Examples include, but are not limited to, Wi-Fi/internet communications, cellular communications, near-field communications, and the like. In the embodiment illustrated in FIG. 6, the wireless communication circuitry 124 alternatively or further includes a Bluetooth® module 126, e.g., in the form of a conventional Bluetooth® controller, that is electrically connected to a conventional Bluetooth® antenna 128 as illustrated by example in FIG. 5. As such, the MCD 102 is configured to conduct wireless communications with the photobiomodulation device 50 according to a conventional Bluetooth® communications protocol. In some embodiments, such wireless communications may be one-way; such that the MCD 102 may only wirelessly transmit information to the photobiomodulation device 50 and the photobiomodulation device 50 may only receive information wirelessly transmitted by the MCD 102, or vice versa, and in other embodiments such wireless communications may be two-way; such that the MCD 102 and the photobiomodulation device 50 may both wirelessly transmit information to, and receive information wirelessly transmitted by, the other.

In some embodiments in which the photobiomodulation device 50 includes wireless (or wired) communication capability as described above, the processor 104 of the MCD 102 is operable to control operation of the device 50 by executing the PBMD application 110 stored in the memory 108. In one embodiment, for example, at least one of the integrated circuits 92 mounted to the circuit board 82 of the device 50 is a conventional timer circuit coupled to the switch 90, and the PBMD application 110 illustratively includes instructions which, when executed by the processor 104, cause the processor 104 to control the wireless communication circuitry 126, 128 to wirelessly transmit one or more signals to the device 50 which carry(s) instructions to activate the timer circuit to cause the timer circuit to turn on and off the switch 90 at a predetermined pulse rate; e.g., 40 Hz. The Bluetooth® controller 96 on-board the device 50 is, in turn, operable to receive such instructions and to control the timer circuit to operate as just described. In other embodiments in which the pulse rate of the timer circuit is programmable, the PBMD application 110 illustratively includes instructions which, when executed by the processor 104, cause the processor 104 to control the wireless communication circuitry 126, 128 to wirelessly transmit one or more signals to the device 50 which carry(s) instructions to activate the timer circuit to cause the timer circuit to turn on and off the switch 90 at a selected pulse rate. In some embodiments, the duty cycle of the timer circuit may be static, e.g., 50%, and in other embodiments the duty cycle may be programmable and selectable as just described with respect to the pulse rate.

In other embodiments, at least one of the integrated circuits 92 mounted to the circuit board 82 of the device 50 may be a conventional processor coupled to, or including, a memory and to the switch 90, and such a memory may include instructions executable by the processor of the device 50 to cause the processor to control operation of the switch 90. In some such embodiments, the pulse rate and/or duty cycle of the irradiation sources 58A-58D may be static and in other embodiments may be selectable as described above.

In any case, the PBMD application 108 illustratively presents a user interface on the display screen 116 via which the user may selectively, i.e., via manual interaction with a touch-selectable interface displayed on the screen 16 and/or via manual selection of a button, switch or key of the MCD 102, control operation of the device 50 including use duration, e.g., 15-minute use intervals. In some embodiments, the PBMD application 108 may also provide for automatic capture of use data, e.g., calendar date, time of day, duration of use, location of use (e.g., via GPS data), etc., user entry of personal data, e.g., name, age, user activity level during use, user physiological and/or psychological state, e.g., hot, cold, calm, nervous, anxious, etc., and/or diagnostic data relating to operation of the device 50 (e.g., in embodiments in which the device 50 is configured to wirelessly transmit such data to the MCD 102).

Figure 7:
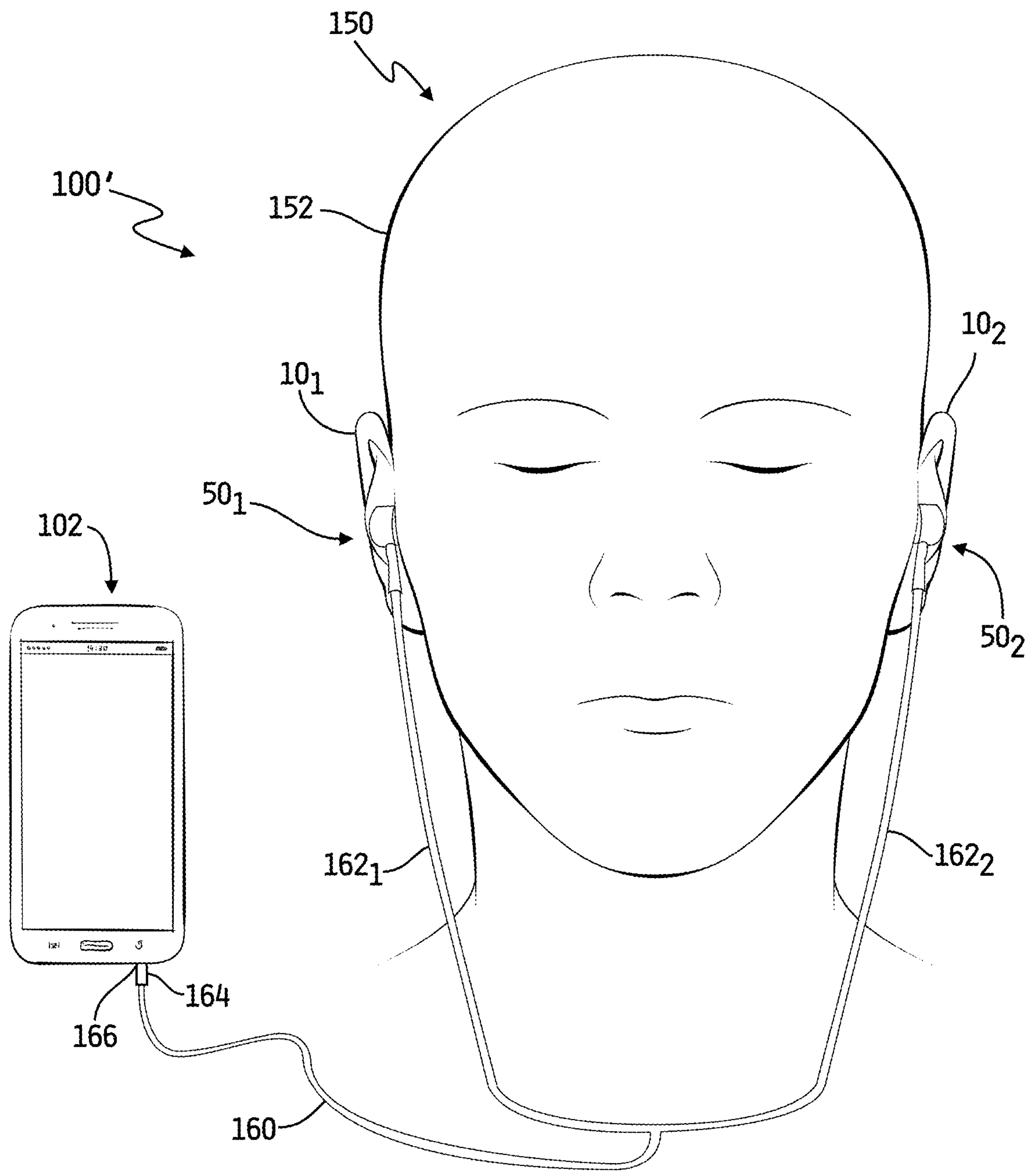
FIG. 7 is a simplified diagram another embodiment of a photobiomodulation system showing a pair of external auditory canal photobiomodulation devices, similar to that illustrated in FIGS. 2A-2D, each placed in transdermal contact with the external auditory meatus of a respective one of a pair of human ears and connected via a wired connection to a mobile communication device, wherein the photobiomodulation devices are controlled by a software application executed by the mobile communication device.

Referring now to FIG. 7, another embodiment is shown of a control photobiomodulation system 100' in which the mobile communication device (MCD) 102 is hard-wire connected, via a wiring harness 160, to two photobiomodulation devices $\mathbf{50}_1$, insertable into one ear $\mathbf{10}_1$, e.g., a right ear on a right side of a head 152 of a human, and $\mathbf{50}_2$, insertable into another ear $\mathbf{10}_2$, e.g., a left ear on a left side of the human head 152. In the illustrated embodiment, the photobiomodulation device $\mathbf{50}_1$ is operatively connected to one end of a wire assembly $\mathbf{162}_1$ of the wiring harness 160, the photobiomodulation device $\mathbf{50}_2$ is operatively connected to one end of another wire assembly $\mathbf{162}_2$ of the wiring harness 160, and the opposite ends of the wire assemblies $\mathbf{162}_1$ and $\mathbf{162}_2$ are merged together and operatively connected to a conventional electrical connector 164 configured to be received in mechanical and electrical engagement with a correspondingly configured port 166 defined on and in the MCD 102. In some embodiments, the MCD 102 is programmed, e.g., as described above, to control operation of the photobiomodulation devices $\mathbf{50}_1$, $\mathbf{50}_2$. In some alternate embodiments, either or both of the photobiomodulation devices $\mathbf{50}_1$, $\mathbf{50}_2$ (or any of the wireless photobiomodulation devices 50 described above) may include some or all of the circuitry required to operate them as described above. It will be understood that whereas two photobiomodulation devices $\mathbf{50}_1$, $\mathbf{50}_2$ are shown hard-wire connected to the MCD 102 in FIG. 7, alternate embodiments are contemplated in which the wiring harness 160 is configured to operatively couple more or fewer photobiomodulation devices to the MCD 102.

Use of the photobiomodulation device 50 illustrated in the attached figures and described herein may be used in either ear or in both ears 10 to provide therapeutic benefit to individuals suffering from any of a number of different physiological and/or psychological conditions. Examples of some such physiological and/or psychological conditions may include, but are not limited to, dementia, Alzheimer's disease, movement disorders generally (e.g., Parkinson's disease, as well as other movement disorders), peripheral inflammatory disorders, pulmonary edema, irritable bowel disorders, functional abdominal pain, digestive problems, chest pain, facial pain, nausea, vomiting, respiratory disorders and related conditions, disturbance of taste, difficulty swallowing, Tinnitus, Vertigo, migraine headaches, muscular tension-type headaches, temporomandibular joint dysfunction (TMJ) including, but not limited to, pain, inflammation, edema of the TMJ's and supporting structure(s), vagal nerve dysfunctions including, but not limited to, low vagal tone, vagal insufficiency, Gastroparesis, Fibromyalgia, Bradycardia, tachycardia and the like, anxiety, depression, autonomic nervous system disorders, whether sympathetic, parasympathetic or a combination thereof, post-traumatic stress disorder (PTSD), attention deficit disorder (ADD, attention deficit and hyperactivity disorder (ADHD), cognitive performance, relaxation, bruxing, teeth clenching, restless leg syndrome, insomnia and/or as an adjunctive for sleep, acute pain conditions, and the like.

Figure 8A:
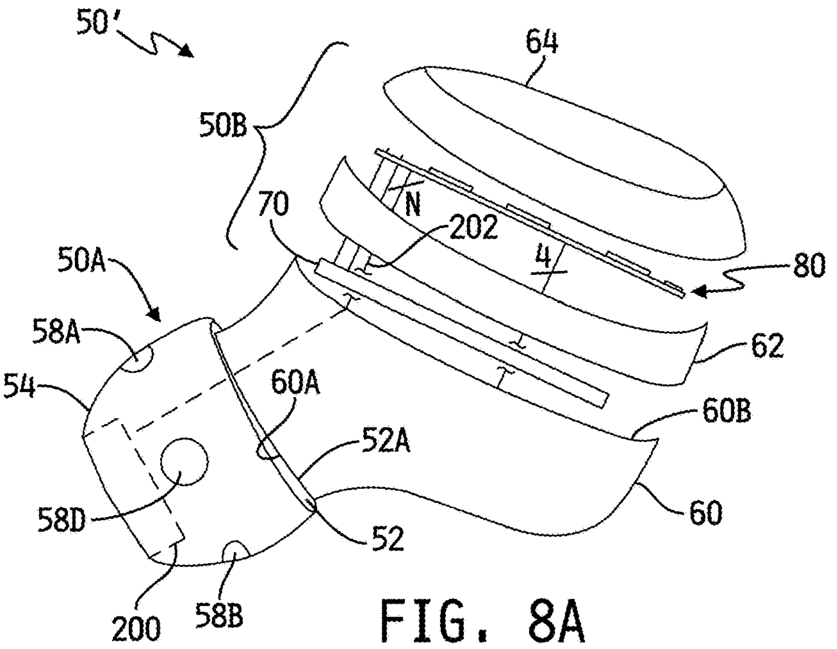
FIG. 8A is a partial assembly view of an embodiment of an external auditory canal photobiomodulation and audio therapy device.
Figure 8B:
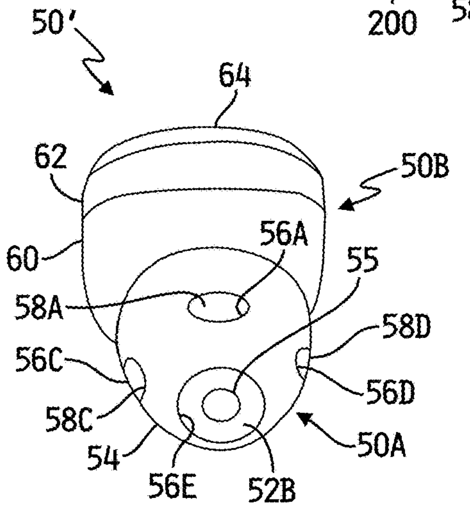
FIG. 8B is an elevated end view of the external auditory canal photobiomodulation and audio therapy device of FIG. 8A.

Referring now to FIGS. 8A and 8B, an embodiment is shown of an external auditory canal photobiomodulation and audio therapy device 50'. The device 50' is identical in many respects to the photobiomodulation device 50 illustrated by example in FIGS. 2A-7, and like numbers are therefore used to identify like components. The external auditory canal photobiomodulation and audio therapy device 50' illustratively differs from the photobiomodulation device 50 in that at least one speaker 200 is mounted within the housing 52 at or adjacent to the end 52B of the housing 52 as depicted by example in FIG. 8A. In the illustrated embodiment, the end 52B of the housing 52 defines an opening 55 therein, and the at least one speaker 200 is positioned relative to the housing 52 such that acoustic waves produced by the at least one speaker 200 exit the opening 55. With the external auditory meatus insertion portion 50A of the device 50' inserted into an ear 10 of a human, so as to place the external auditory meatus insertion portion 50A of the device 50' in transdermal contact with the external auditory meatus of the ear 10 as described above with respect to FIGS. 5 and 7, acoustic waves exiting the at least one speaker 200 pass through the opening 55 of the housing 52 and move through the external auditory meatus 18 toward a tympanic membrane 20 of the ear 10 (see, e.g., FIG. 1B). In the illustrated embodiment, only a single speaker 200 is shown and only a single opening 55 is shown, although it will be understood that in alternate embodiments the at least one speaker 200 may include multiple speakers and/or the opening 55 may include multiple openings in and/or adjacent to the end 52B of the housing 52.

In any case, the at least one speaker is electrically connected via a number, N, of signal paths 202 to one or more components of the electrical circuit 80 mounted to the circuit board 82, wherein N may be any positive integer. In one embodiment, at least one of the integrated circuits 92 is or includes conventional speaker driver circuitry configured to be responsive to input audio signals to drive the at least one speaker 200 to produce corresponding acoustic waves. In some embodiments, at least one of the integrated circuits 92 may be or include a conventional processor, e.g., a microprocessor, controller, or the like, and at least one memory device having instructions stored therein that are executable by the processor to control operation of the irradiation sources 58A-58D and operation of the at least one speaker 200 as described by example below.

In some embodiments, the memory device may have stored therein one or more audio files, and the processor may be operable in such embodiments to provide the audio signals from at least one of such audio files to the speaker driver circuitry described above. In some such embodiments, the electrical circuit 80 may include circuitry to control operation of the irradiations sources 58A-58B as also described above. Alternatively or additionally, audio signals from one or more audio files may be provided to the speaker driver circuitry from one or more sources external to the device 50' and/or control signals for controlling operation of the irradiation sources 58A-58D may be provided to the electrical circuitry 80 from one or more sources external to the device 50'. An example of one such external source is a mobile communication device 102', as illustrated by example in FIG. 9.

Figure 9:
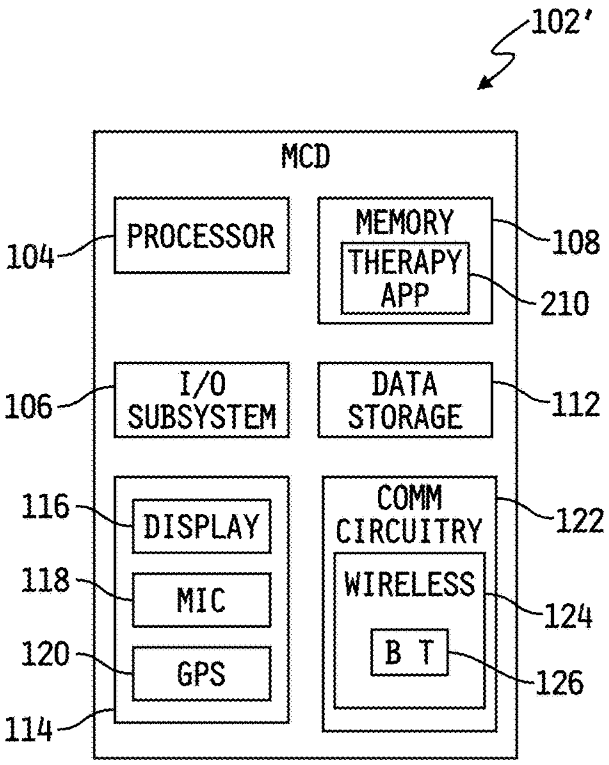
FIG. 9 is a simplified schematic block diagram of another embodiment of the mobile communication device of FIG. 5.

In the embodiment illustrated in FIG. 9, the mobile communication device 102' is identical in many respects to the mobile communication device 102 illustrated in FIG. 6 and described in detail above, and like numbers are therefore used to identify like components. The mobile communication device 102' may communicate wirelessly with one or more external auditory canal photobiomodulation and audio therapy devices 50' as described above with respect to FIG. 5 and/or the mobile communication device 102' may communicate with one or more external auditory canal photobiomodulation and audio therapy devices 50' as described above with respect to FIG. 7.

The mobile communication device 102' illustratively differs from the mobile communication device 102 in that the memory 108 has a therapy application 210 stored therein in the form of instructions executable by the processor 104 to control operation of the external auditory canal photobiomodulation and audio therapy device(s) 50', i.e., to control operation of the irradiation sources 58A-58B and to control operation of the at least one speaker 200. One example of such a therapy application is illustrated by example in FIG. 10, which will be described in detail below.

In some embodiments in which the mobile communication device 102' controls operation of the at least one speaker 200 as described above, the memory 108 and/or the data storage 112 may have one or more audio files stored therein, e.g., stored by action of a user of the mobile communication device 102' and/or stored automatically by operation of the therapy application 210. In such embodiments the processor 104 is illustratively operable to control operation of the at least one speaker 200 by transmitting, e.g., wirelessly or via wired connection, audio signals from at least one predetermined, or user selected, one of the stored one or more audio files to the speaker driver circuitry included in the integrated circuits 92 as described above. The speaker driver circuitry, in turn, is responsive to the input audio signals to drive the at least one speaker 200 in a conventional manner to cause the at least one speaker 200 to produce acoustic waves corresponding to the input audio signals. Alternatively or additionally, the mobile communication device 102' may be configured to access one or more audio files from an external source, e.g., via the therapy application 210 and/or via one or more other conventional audio content access software applications executable by the processor 104, either or both of which may be configured to download or stream the one or more audio files from an external audio file service or other private or public source of audio files. In the former case, the processor 104 of the mobile communication device 102' may access any such external audio file service automatically or via user selection under the direction of the therapy application 210, and in the latter case the processor 104 may access any such external audio file service via user control and selection under the direction of the one or more other conventional audio content access software applications executable by the processor 104. In either case the processor 104 may access the one or more audio files in a conventional manner, e.g., via the Internet and/or via a private network using the wireless communication circuitry 124.

Any of the one or more audio files may illustratively include a single, constant frequency or a structured or random pattern of one or multiple frequencies. In applications which include two external auditory canal photobiomodulation and audio therapy devices 50', i.e., one inserted in each ear 10, the audio signals sent to one device 50' may be the same or different from the audio signals sent to the other device 50'. Generally, the frequency or frequencies of audio signals within the one or more audio files will be within the conventional range of frequencies detectable to humans, i.e., 20 Hz-20 k Hz, although it will be understood that this disclosure contemplates audio files in which the frequency or frequencies of audio signals within the one or more audio files may be outside of this range, examples of which may include, but are not limited to, ultrasound and/or infrasound.

Each of the one or more audio files may have or include any content without limitation. Examples of content of the audio signals of any such audio file, may be or include, but are not limited to, at least one of single frequency tone signals, multiple frequency tone signals, music signals, noise signals, beat signals, binaural beat signals and the like.

The term "acoustics" relates to the generation, propagation and reception of acoustic waves, wherein "acoustic waves" may include any of mechanical waves, vibrations, sound, ultrasound (i.e., sound waves with frequencies above the upper audible limit of human hearing) and infrasound (i.e., sound waves with frequencies below the lower audible limit of human hearing). The interaction of acoustic waves with biological tissue generally fall into three categories: (1) diffraction, (2) interference and (3) reflection. While the foregoing can be singular occurrences, acoustic waves generated by the one or more speakers 200 of one or two inserted external auditory canal photobiomodulation and audio therapy devices 50' (as described above) affect the arterial branches 24 and peripheral nerve branches 16 of cranial nerves located below the dermis 22 of the external auditory meatus 18 of the human ear(s) 10, as well as the surrounding tissues, via a combination of diffraction, interference and reflection.

Diffraction, for purposes of this disclosure, is the bending of acoustic waves around an object through an aperture which effectively becomes a second source of the propagating acoustic wave. This can be due to the addition of different waves that travel by paths of different lengths producing a complex pattern of varying intensity. Interference, for purposes of this disclosure, is a phenomenon in which two acoustic waves are superimposed on one another to form a resulting wave of greater, lower or the same amplitude. Constructive and destructive interference can result from interactions of such waves generated by the same source. Reflection, for purposes of this disclosure, is a change in direction of an acoustic wave at an interface with a surface. Generally, the incident angle is equal to the angle of reflection. One effect of acoustic wave reflection is an echo.

In one example embodiment, the audio signals contained in at least one audio file includes binaural beats. In this embodiment two different tones/frequencies are presented independently to the right and left ear. The rate of fluctuation as interpreted by the human brain depends on the separation of frequency between the two tones/frequencies. The brain, as a result, will interpret the two signals as a third tone of constant, rhythmic frequency. The brain follows this constant, rhythmic frequency and produces brainwaves of the same frequency; sometimes referred to as a Frequency Following Response (FFR) or "entrainment." Binaural beat perception originates in the brainstem's inferior colliculi (IC) and superior olivary complex (SOC). The IC is a part of the midbrain that serves as a main auditory center and acts as the channel for most auditory signals in the human body. The SOC is a collection of brainstem nuclei which also functions in the ascending and descending auditory pathway.

Therapy treatment with binaural beats effectively promotes functional connectivity and electrical brain activity, and reduces pain intensity, analgesic use, heart rate variability, perceived stress and differential patterns of brain connectivity. Brain stimulation by both light (via control of the irradiation source(s) 58A-58D as described above) and binaural beats modulates both alpha and sensorimotor rhythm (SMR) brain wave activities. Alpha brain waves are neural oscillations in the frequency range of 8-12 Hz. Alpha waves are predominately recorded from the occipital lobes during wakeful relaxation, and are diminished with open eyes, drowsiness and sleep. Increasing alpha waves promotes relaxation and reduces anxiety. SMR brainwaves are in the frequency range of 12-15 Hz, and are associated with a calm but alert mental state. Increasing SMR brainwaves promotes reductions of anxiety, depression and insomnia, and improved mood, focus and well-being.

In another example embodiment, the audio signals contained in at least one audio file includes noise. In this embodiment, the noise may be introduced into one or both ears. In one specific implementation, the audio signals contained in at least one audio file includes pink noise. Pink noise represents most or all of the audible frequencies but lower frequencies are amplified while higher frequencies are diminished. Examples of pink noise include tides, waves crashing on the beach, leaves rustling in the trees, rain falling, heartbeats, firing of single neurons, and single-molecule connectivity. Therapy treatment with pink noise effectively synchronizes brain waves so as to reduce brain wave complexity, and thereby promote relaxation, induce more stable sleep and thus improve sleep quality.

Alternatively or additionally, the audio signals contained in at least one audio file may include brown noise. Brown noise has a spectral density that is inversely proportional to f2, meaning that it has higher intensity at lower frequencies (more so than pink noise), and its intensity decreases by 6 dB per octave. Brown noise has a soft quality when compared to pink or white noise, and can be generated by adding together random samples of white noise. Therapy treatment with brown noise is similar to that of pink noise described above.

Alternatively or additionally still, the audio signals contained in at least one audio file may include white noise. White noise is a random noise signal characterized by equal intensity at all frequencies (20 Hz-20 kHz). White noise has found use as a privacy enhancer, and is useful as a sleep aid and as a mask for tinnitus. Therapy treatment with white noise effectively improves mood and performance but can decrease cognitive performance; however, white noise treatment does appear to improve cognitive performance in people with attention deficit hyperactivity disorder (ADHD).

Various combinations of the foregoing may also be used to treat specific conditions. As one non-limiting example, combining binaural beats with pink noise may reduce post-surgical pain medication consumption.

Figure 10:
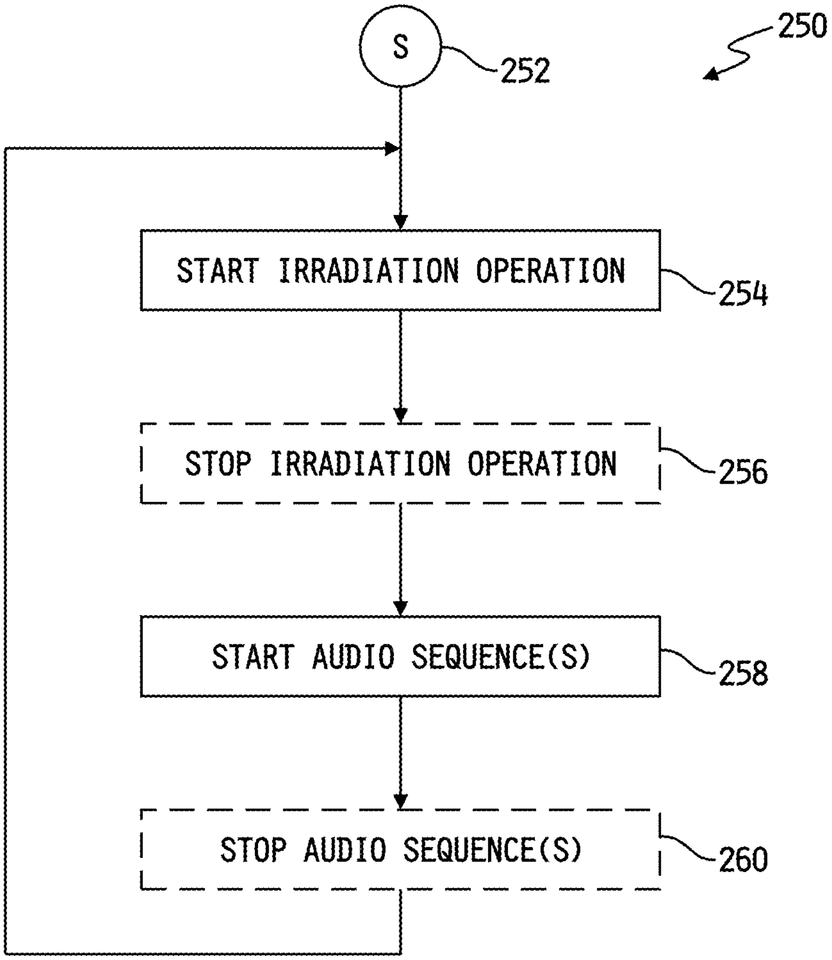
FIG. 10 is a flowchart illustrating an embodiment of a process for controlling operation of the external auditory canal photobiomodulation and audio therapy device of FIG. 8.

Referring now to FIG. 10, a flowchart is shown of a process 250 for controlling one or more of the external auditory canal photobiomodulation and audio therapy devices 50', and is thus one example of the therapy application 210 stored in the memory 108 of the mobile communication device 102' and executable by the processor 104. In alternate embodiments in which the mobile communication device 102' is not included, the electrical circuit 80 may include one or more circuits, e.g., at least one processor and memory or other application specific circuits, configured to execute the process 250 illustrated in FIG. 10. In any case, the process 250 will be described as being executed by the processor 104, it being understood that the process 250 in alternate embodiments may be implemented and executed completely by the electrical circuit 80 or by a combination of the processor 104 and the electrical circuit 80.

The process 250 begins at step 252, and thereafter at step 254 the processor 104 is operable to start irradiation operation, i.e., control the irradiation source(s) 58A-58D, to irradiate the inserted external auditory canal photobiomodulation and audio therapy device(s) 50' as described above. In some embodiments of the process 250, step 256 may be included in which the processor 104 is operable to stop irradiation by the irradiation source(s) 58A-58D prior to executing step 258 in which the processor 104 is operable to start the audio sequence(s); i.e., to send or active one or more audio files so as to control the at least one speaker(s) 200 to produce corresponding acoustic waves as described above. In such embodiments, the process 250 may also include step 260 in which the processor 104 is operable to step the audio sequence(s). In such embodiments, the irradiation therapy, i.e., with the irradiation source(s) 58A-58D is alternated with the audio therapy. In some alternate embodiments, the audio therapy may occur prior to the irradiation therapy such that steps 258 and 260 may precede steps 254 and 256.

In alternate embodiments of the process 250, step 256 and 260 may be omitted such that the irradiation therapy and the audio therapy may be conducted simultaneously. In such embodiments, the irradiation therapy or the audio therapy may be started before the other or they may be started simultaneously. The process 250 may loop so as to continually execute for some predetermined time period or until stopped by a user.

Figure 11A:
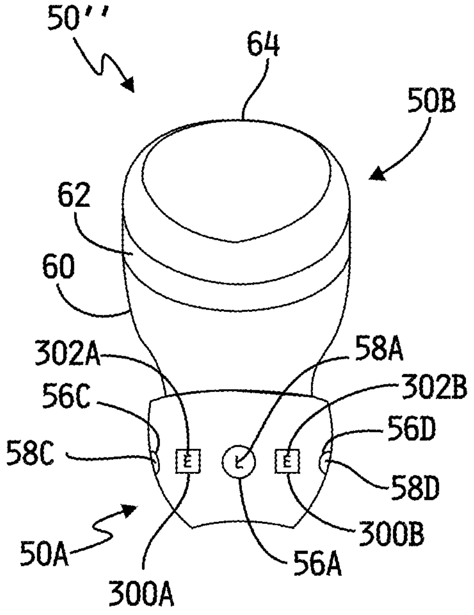
FIG. 11 includes FIGS. 11A-11D which illustrate various views of an embodiment of an external auditory canal therapy device.
Figure 11B:
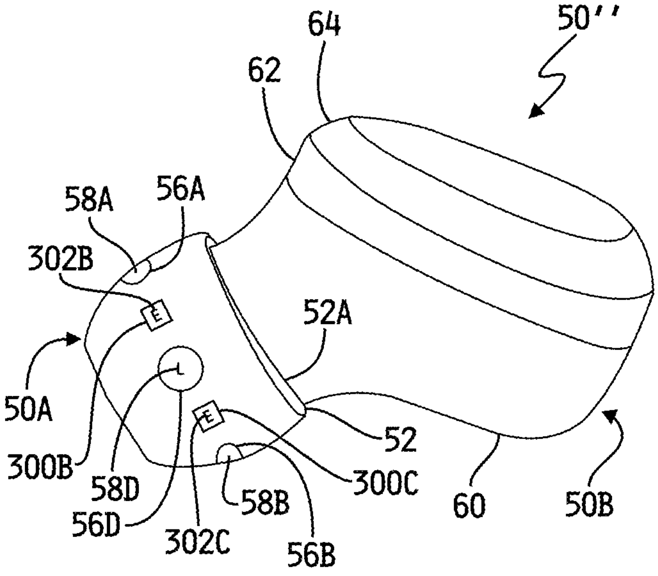
Figure 11C:
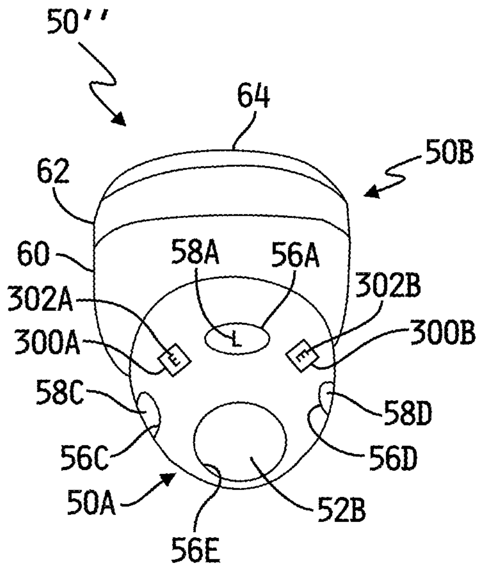
Figure 11D:
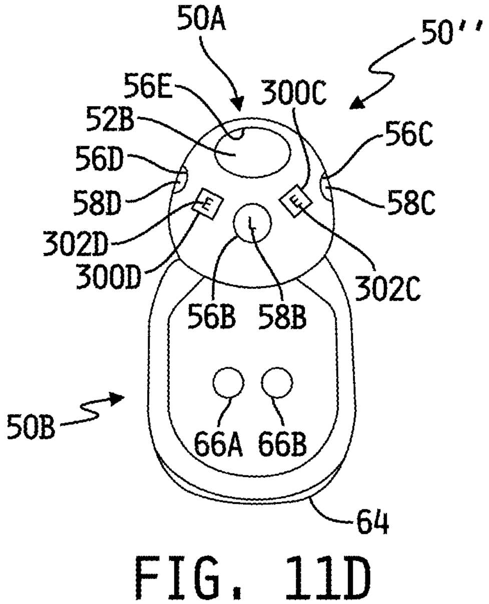
Figure 12:
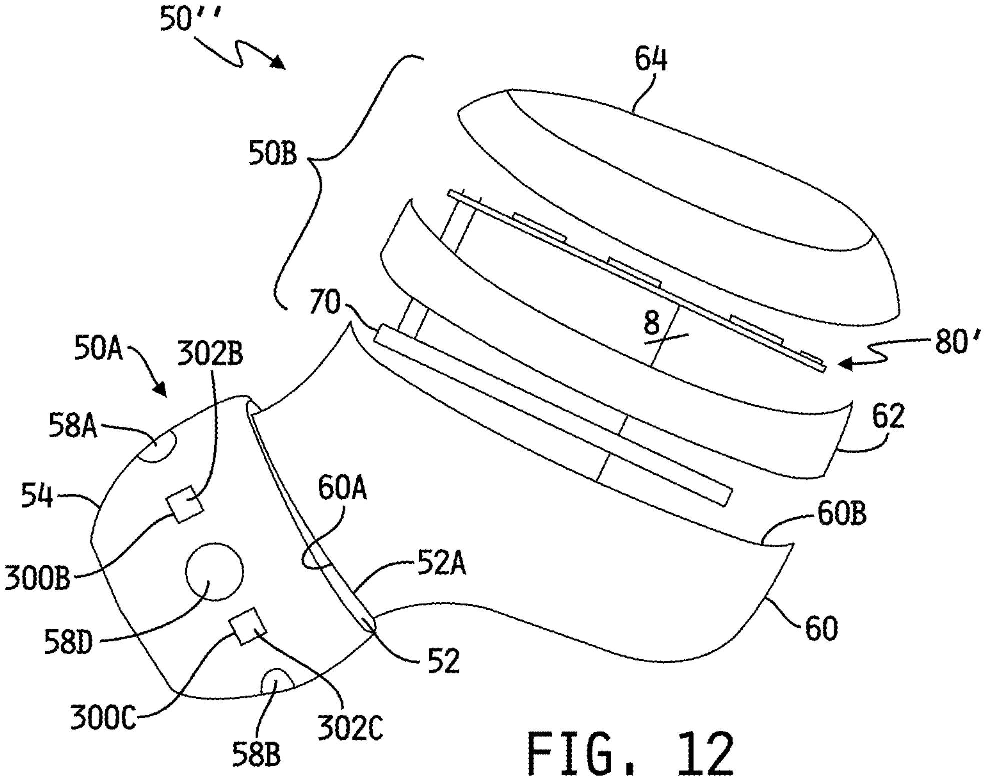
FIG. 12 is a partial assembly view of the external auditory canal therapy device of FIG. 11.

Referring now to FIGS. 11A-12, an embodiment is shown of an external auditory canal therapy device 50". The device 50" is identical in many respects to the photobiomodulation device 50 illustrated by example in FIGS. 2A-7, and like numbers are therefore used to identify like components. The external auditory canal therapy device 50" illustratively differs from the photobiomodulation device 50 in that, in addition to the one or more irradiation sources, at least one electrically conductive electrode is mounted to and within the housing 52 of the external auditory meatus insertion portion 50A of the device 50" and is/are controlled by the electrical circuit 80 separately from the irradiation source(s). In the embodiment illustrated in FIGS. 11A-12, for example, housing 52 and ear tip or cap 54 (in embodiments which include the ear tip or cap 54) define a number of openings therethrough each sized to receive therein an electrically conductive electrode, such that, with the external auditory meatus insertion portion 50A inserted into the external auditory canal, an electrically conductive surface of each of the number of electrodes faces and contacts a respective portion of the entrance opening 14 and/or at least a portion of the external auditory meatus 18 adjacent thereto. In alternate embodiments, the housing 52 and ear tip or cap 54 (in embodiments which include the ear tip or cap 54) may not define openings per se in which a respective electrically conductive electrode is received, but may instead define locations at or in which a respective irradiation source is mounted. In any case, each of the number of irradiation sources illustratively directs radiation produced thereby toward a respective one or more of the peripheral branches of one or more of the cranial nerves 16 and/or toward a respective one or more arterial branches 24 extending about the periphery of the entrance opening 14 and at least partially into the external auditory meatus 18 beneath the dermis 22, and each of the number of electrically conductive electrodes, in contact with the dermis 22 of the entrance opening 14 and at least partially into the external auditory meatus 18, illustratively directs electrical stimulation signals toward a respective one or more of the peripheral branches of one or more of the cranial nerves 16 and/or toward a respective one or more arterial branches 24 extending about the periphery of the entrance opening 14 and at least partially into the external auditory meatus 18 beneath the dermis 22.

In the embodiment illustrated in FIGS. 11A-11D and 12 in which four openings 56A-56D are spaced equidistant from one another radially about the housing 52 and ear tip or cap 54, and in which four corresponding irradiation sources 58A-58D are inserted into a respective one of the openings 56A-56D as described above, four additional openings 300A-300D are likewise spaced equidistant from one another radially about the housing 52 and ear tip or cap 54 such that each opening 300A-300D is positioned between two adjacent openings 56A-56D. Four corresponding electrically conductive electrodes 302A-302D are inserted into a respective one of the openings 300A-300D so as to be positioned in contact the dermis 22 radially about the external auditory meatus 18 when the external auditory meatus insertion portion 50A is inserted into the external auditory canal or meatus 18. In this embodiment, the device 50" is illustratively orientable to position each of the irradiation sources 58A-58D and each of the electrically conductive electrodes 302A-302D opposite to, and facing, the peripheral branches of a respective at least one of the cranial nerves 16 and/or of a respective at least one of the arterial branches in or adjacent to the region containing the cranial nerves 16 as described above. In alternate embodiments, the device 50" may include more or fewer irradiation sources and/or may include more or fewer electrically conductive electrodes, and/or the irradiation source(s) or electrically conductive electrode(s) may or may not be positioned radially about the housing 52.

In the embodiment illustrated in FIGS. 11A-11D, the electrical circuit 80' illustratively includes the same circuitry as the electrical circuit 80 illustrated in FIG. 4 and described above, and further includes additional circuitry for controlling operation of the one or more electrically conductive electrodes, e.g., 302A-302D. The electrical requirements, including one or more of voltage/current levels, switching frequency, pulse duration, therapy duration, etc., for directing electrical stimulation signals to the peripheral branches of one or more of the cranial nerves 16 and/or to one or more arterial branches 24 extending about the periphery of the entrance opening 14 and at least partially into the external auditory meatus 18 via electrical contact between the electrically conductive electrode(s) and the dermis 22, may be different than the electrical requirements for operating the irradiation source(s). In this regard, the irradiation source(s) and the electrically conductive electrode(s) will generally be operated separately from one another, e.g., either solely by the electrical circuit 80' or by a combination of the electrical circuit 80' and an external device such as the MCD 102 illustrated by example in FIGS. 6 and 9. In the embodiment illustrated in FIGS. 11A-12 which includes four irradiation sources 58A-58D and four electrically conductive electrodes 302A-302D, eight electrical conductors are thus shown extending between the electrical circuit 80' and the housing 52 each electrically connected between the electrical circuit 80' and a respective one of the four irradiation sources 58A-58D and four electrically conductive electrodes 302A-302D. With the one or more electrically conductive electrodes being controlled separately from the one or more irradiation sources, one of the circuit components of the electrical circuit 80 may thus require duplication in the electrical circuit 80'. For example, additional electrical terminals 86 may be provided to electrically connect between the electrical circuit 80' and the electrically conductive electrode(s), additional resistors 88 (with different resistance value(s) in some embodiments) may be provided to established desired levels of electrical current provided to the electrically conductive electrode(s), an additional switch 90 (or switches) may be provided to control switching of current pulses the electrically conductive electrode(s), and in some embodiments additional or alternative integrated circuits 92 may be provided to control operation of the switch(es) 90, e.g., to control switching frequency, duty cycle, switching duration, etc.

In some embodiments which include one or more electrically conductive electrodes, e.g., as illustrated by example in FIGS. 11A-11B, such electrodes are illustratively controlled to operate as conventional transcutaneous electrical nerve stimulation (TENS) devices, albeit positioned relative to a human in an unconventional manner in contact with the dermis 22 of and about the external auditory meatus 18. In one example embodiment, which should not be considered to be limiting in any way, the electrically conductive electrodes 302A-302D are controlled together in accordance with the following example therapy sequence:

Repeat sequentially for P time units with a rest or pause time between each repeated pattern (in which no electrical stimulation signals are applied) of Q time units. The total therapy time is R time units.

1. Apply S volts to electrodes at T hertz for U time units.
2. Rest or pause V time units.
3. Apply S volts to electrodes at W hertz for U time units.
4. Rest or pause V time units.

Example values of variables P-V are the following, although it will be understood that in other implementations one or more of P-V may take on different values:

P=15 minutes.
Q=1 minute.
R=2 hours.
S=4.2 volts.
T=1 Hz.
U=1 millisecond.
V=2000 milliseconds.

In some embodiments which include multiple electrically conductive electrodes, all such electrodes are controlled identically and simultaneously such that all operate the same as just described in the foregoing example. In alternate embodiments, the electrical circuit 80' may be configured to control one or more of the electrodes differently in one or more respects, e.g., different applied current, frequency, duty cycle and/or duration, etc., than other(s) of the electrodes. As one non-limiting example, the above sequence (or a different sequence) may be alternatingly applied to different subsets of the electrodes. As another non-limiting example in which the device 50" includes four separate electrodes ad depicted by example in FIGS. 11A-12, the following may be repeated sequentially for P time units with a rest or pause time between each repeated pattern (in which no electrical stimulation signals are applied) of Q time units, wherein the total therapy time is R time units:

1. Apply S volts to electrode 302A at T hertz for U time units.
2. Rest or pause V time units.
3. Apply S volts to electrode 302B at T hertz for U time units.
4. Rest or pause V time units.
5. Apply S volts to electrode 302C at T hertz for U time units.
6. Rest or pause V time units.
7. Apply S volts to electrode 302D at T hertz for U time units.
8. Rest or pause V time units.
9. Apply S volts to electrode 302A at W hertz for U time units.
10. Rest or pause V time units.
11. Apply S volts to electrode 302B at W hertz for U time units.
12. Rest or pause V time units.
13. Apply S volts to electrode 302C at W hertz for U time units.
14. Rest or pause V time units.
15. Apply S volts to electrode 302D at W hertz for U time units.
16. Rest or pause V time units.

Example values of variables P-W are the following, although it will be understood that in other implementations one or more of P-W may take on different values:

P=15 minutes.
Q=1 minute.
R=4 hours.
S=4.2 volts.
T=1 Hz.
U=1 millisecond.
V=2000 milliseconds.
W=10 Hz.

In some alternate embodiments, the electrical circuit 80' may be configured to control the electrodes sequentially in a pattern, examples of which may include, but are not limited to, in a radial pattern, e.g., radially about the external auditory meatus 18, in a diametrically opposite pattern, e.g., electrodes 302A and 302D may fire together followed by electrodes 302B and 302C firing together, in a grouped pattern, e.g., electrodes 302A and 302B fire together followed by electrodes 302C and 302D firing together, etc. In some such embodiments, the electrodes or electrode groups may be controlled with identical electrical properties, although in alternate embodiments the electrodes or electrode groups may be controlled with different electrical properties, e.g., different applied current, frequency, duty cycle and/or duration, etc. In any case, the device 50" may be implemented for use in a single ear as illustrated by example in FIG. 5 or as a pair; one in each ear as illustrated by example in FIG. 7.

Figure 13:
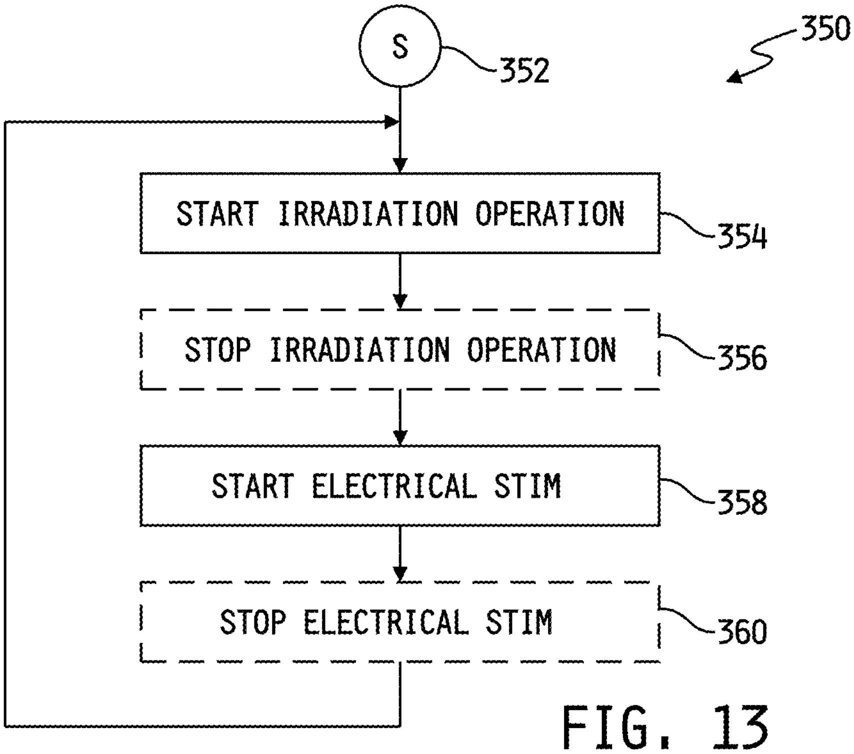
FIG. 13 is a flowchart illustrating an embodiment of a process for controlling operation of the external auditory canal therapy device of FIGS. 11 and 12.

Referring now to FIG. 13, a flowchart is shown of an embodiment of a process 350 for controlling one or more of the external auditory canal therapy devices 50", and is thus another one example of the therapy application 210 stored in the memory 108 of the mobile communication device 102' and executable by the processor 104. In alternate embodiments in which the mobile communication device 102' is not included, the electrical circuit 80' may include one or more circuits, e.g., at least one processor and memory or other application specific circuits, configured to execute the process 350 illustrated in FIG. 13. In any case, the process 350 will be described as being executed by the processor 104, it being understood that the process 350 in alternate embodiments may be implemented and executed completely by the electrical circuit 80' or by a combination of the processor 104 and the electrical circuit 80'.

The process 350 begins at step 352, and thereafter at step 354 the processor 104 is operable to start an irradiation operation, i.e., to control the irradiation source(s) 58A-58D, to irradiate the external auditory meatus 18 via the inserted external auditory canal therapy device(s) 50" as described above. In some embodiments of the process 350, step 356 may be included in which the processor 104 is operable to stop the irradiation sequence(s) by turning off or disabling irradiation by the irradiation source(s) 58A-58D prior to executing step 358 in which the processor 104 is operable to start an electrical stimulation operation, i.e., to control the electrically conductive electrode(s) 302A-302D, to electrically stimulate the external auditory meatus 18 via the inserted external auditory canal therapy device(s) 50" as also described above. In such embodiments, the process 350 may also include step 360 in which the processor 104 is operable to stop the electrical stimulation sequence(s) by turning off or disabling electrical stimulation by the electrode(s) 302A-302D. In such embodiments, the irradiation therapy, i.e., with the irradiation source(s) 58A-58D is alternated with the electrical stimulation therapy, i.e., via the electrically conductive electrodes 302A-302D. In some alternate embodiments, the electrical stimulation therapy may occur prior to the irradiation therapy such that steps 358 and 360 may precede steps 354 and 356.

In alternate embodiments of the process 350, steps 356 and 360 may be omitted such that the irradiation or photobiomodulation therapy and the electrical stimulation therapy may be conducted simultaneously. In such embodiments, the irradiation therapy or the electrical stimulation therapy may be started before the other or they may be started simultaneously. In some embodiments, the process 350 may loop so as to continually execute for some predetermined time period or until stopped by a user.

Figure 14A:
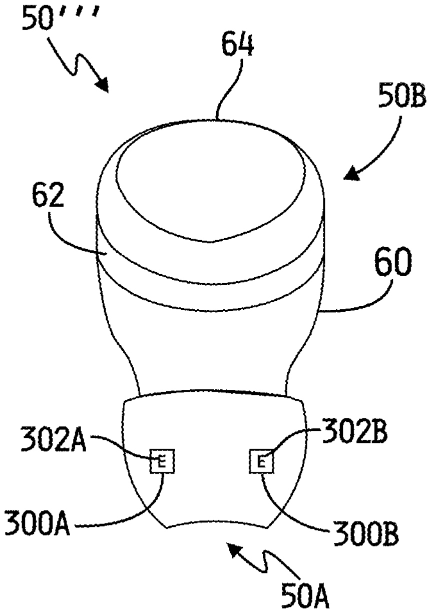
FIG. 14 includes FIGS. 14A-14D which illustrate various views of another embodiment of an external auditory canal therapy device.
Figure 14B:
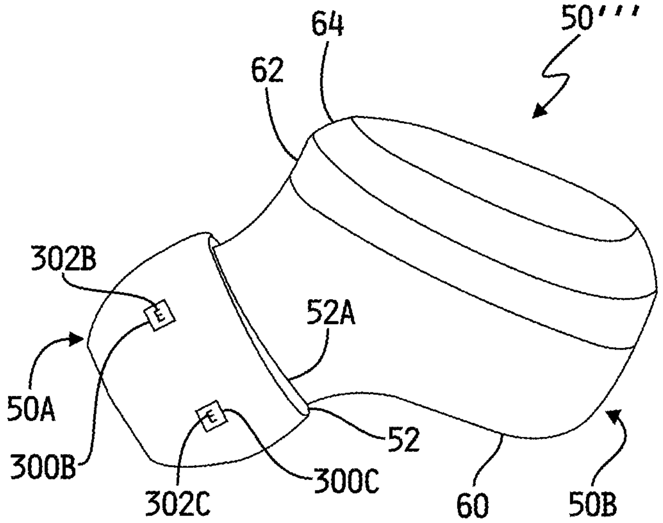
Figure 14C:
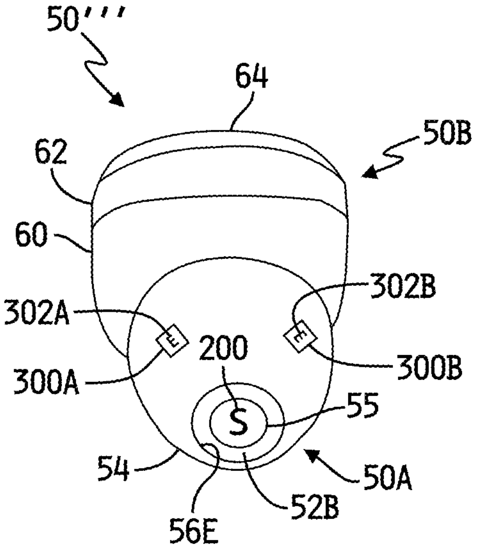
Figure 14D:
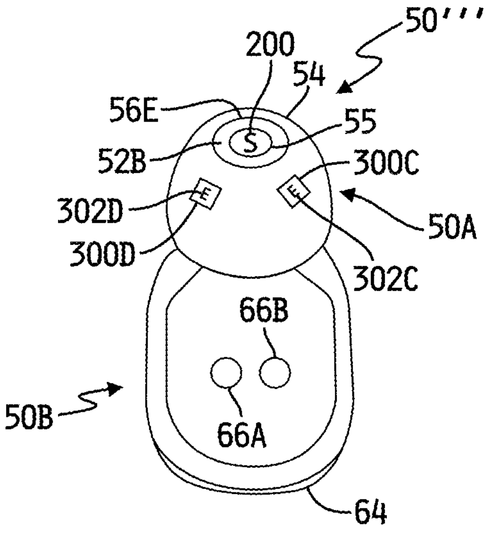
Figure 15:
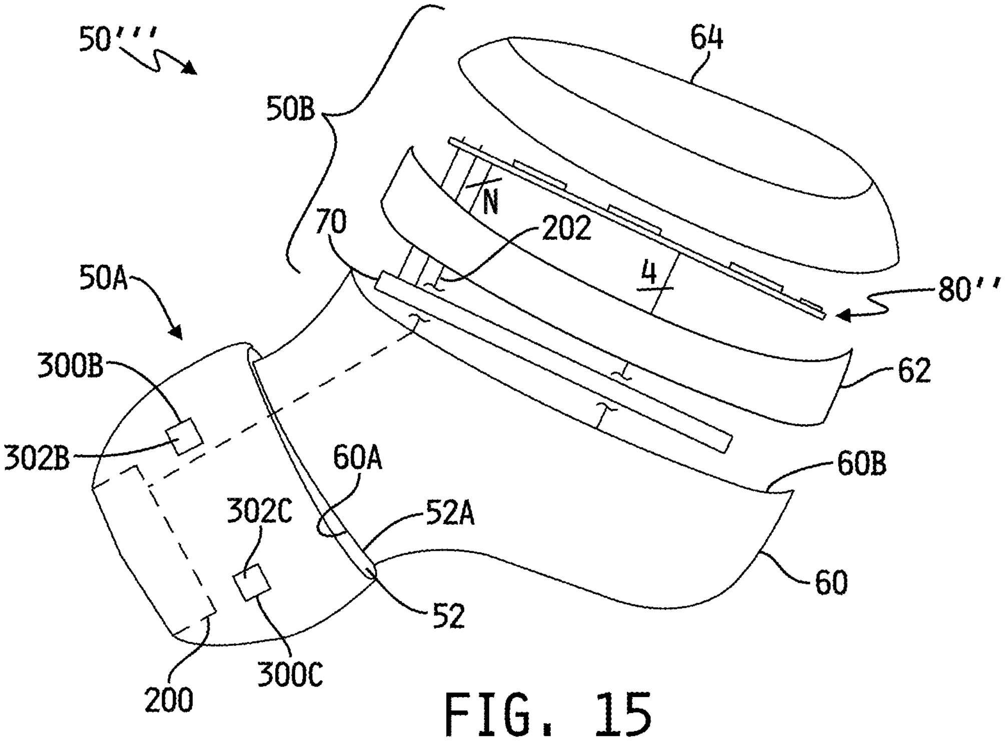
FIG. 15 is a partial assembly view of the external auditory canal therapy device of FIG. 14.

Referring now to FIGS. 14A-15, another embodiment is shown of an external auditory canal therapy device 50"'. The device 50"'is identical in many respects to the photobiomodulation and audio therapy device 50' illustrated by example in FIGS. 2A-7 and the external auditory canal therapy device 50" illustrated by example in FIGS. 11A-12, and like numbers are therefore used to identify like components. The external auditory canal therapy device 50"' illustratively differs from the devices 50' and 50" in that the irradiation sources 58A-58D are omitted such that the device 50"' includes one or more electrically conductive electrodes and one or more speakers 200, each as illustrated by example in the attached figures and described above. In this embodiment, the electrical circuit 80" depicted in FIG. 15 includes circuitry described above for controlling, also as described above, the one or more electrically conductive electrodes, e.g., electrodes 302A-302D, and circuitry described above for controlling, also as described above, the one or more speakers 200.

Figure 16:
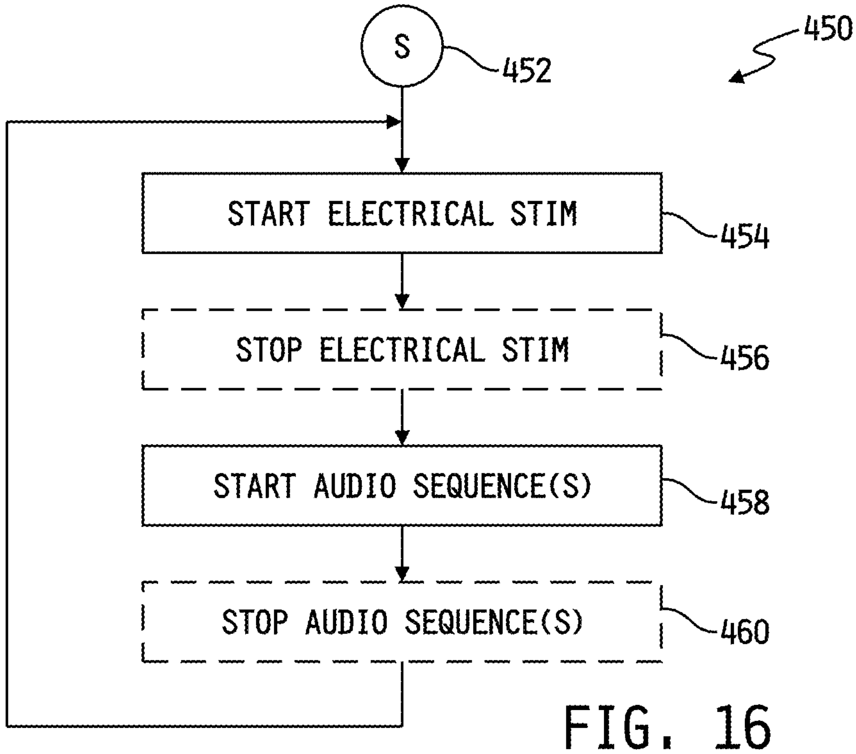
FIG. 16 is a flowchart illustrating an embodiment of a process for controlling operation of the external auditory canal therapy device of FIGS. 14 and 15.

Referring now to FIG. 16, a flowchart is shown of another embodiment of a process 450 for controlling one or more of the external auditory canal therapy devices 50"', and is thus yet another example of the therapy application 210 stored in the memory 108 of the mobile communication device 102' and executable by the processor 104. In alternate embodiments in which the mobile communication device 102' is not included, the electrical circuit 80" may include one or more circuits, e.g., at least one processor and memory or other application specific circuits, configured to execute the process 450 illustrated in FIG. 16. In any case, the process 450 will be described as being executed by the processor 104, it being understood that the process 450 in alternate embodiments may be implemented and executed completely by the electrical circuit 80" or by a combination of the processor 104 and the electrical circuit 80".

The process 450 begins at step 452, and thereafter at step 454 the processor 104 is operable to start electrical stimulation operation, i.e., to control the electrically conductive electrode(s) 302A-302D, to electrically stimulate the external auditory meatus 18 via the inserted external auditory canal therapy device(s) 50"' as also described above. In such embodiments, the process 450 may also include step 456 in which the processor 104 is operable to stop the electrical stimulation sequence(s) by turning off or disabling electrical stimulation by the electrode(s) 302A-302D prior to executing step 458 in which the processor 104 is operable to start the audio sequence(s); i.e., to send or active one or more audio files so as to control the at least one speaker(s) 200 to produce corresponding acoustic waves as described above. In such embodiments, the process 450 may also include step 460 in which the processor 104 is operable to stop the audio sequence(s). In such embodiments, the electrical stimulation therapy, i.e., via the electrically conductive electrodes 302A-302D, is alternated with the audio therapy. In some alternate embodiments, the audio therapy may occur prior to the electrical stimulation therapy such that steps 458 and 460 may precede steps 454 and 456.

In alternate embodiments of the process 450, steps 456 and 460 may be omitted such that the electrical stimulation therapy and the audio therapy may be conducted simultaneously. In such embodiments, the electrical stimulation therapy or the audio therapy may be started before the other or they may be started simultaneously. In some embodiments, the process 450 may loop so as to continually execute for some predetermined time period or until stopped by a user.

Figure 17A:
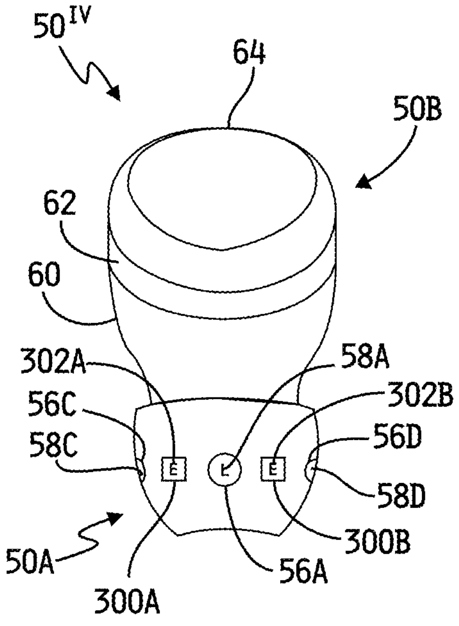
FIG. 17 includes FIGS. 17A-17D which illustrate various views of yet another embodiment of an external auditory canal therapy device.
Figure 17B:
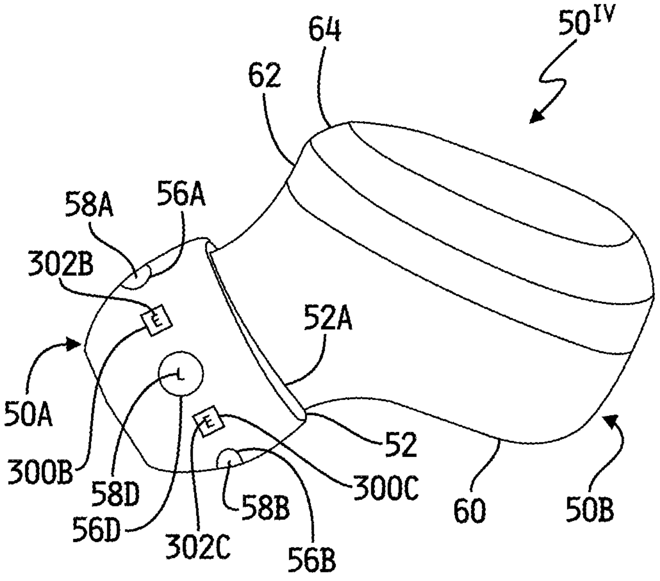
Figure 17C:
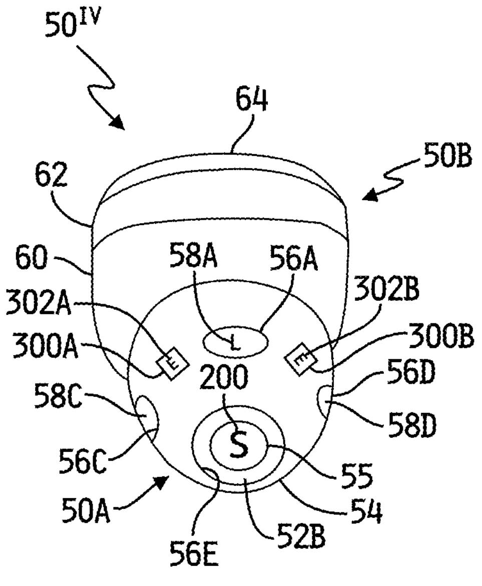
Figure 17D:
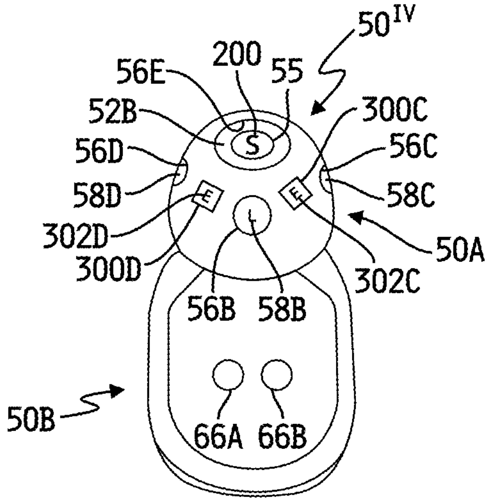
Figure 18:
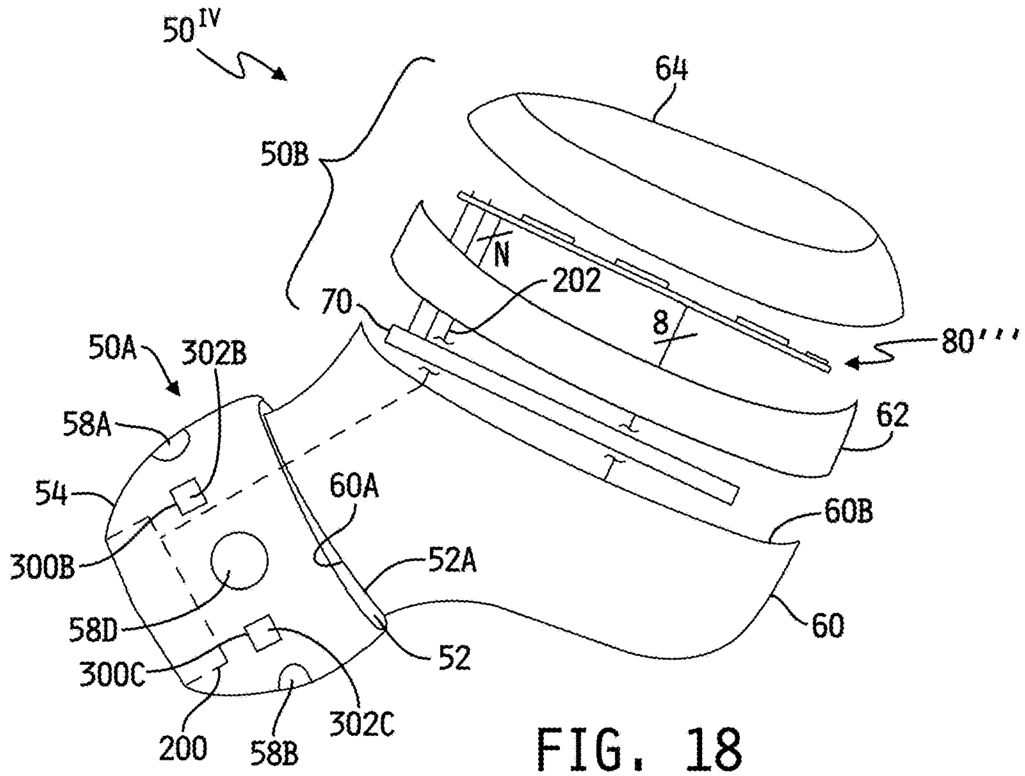
FIG. 18 is a partial assembly view of the external auditory canal therapy device of FIG. 17.

Referring now to FIGS. 17A-18, yet another embodiment is shown of an external auditory canal therapy device 50$^{IV}$. The device 50$^{IV}$ is identical in many respects to the photobiomodulation and audio therapy device 50' illustrated by example in FIGS. 2A-7 and the external auditory canal therapy devices 50" and 50"' illustrated by example in FIGS. 11A-12 and 14A-15 respectively, and like numbers are therefore used to identify like components. The external auditory canal therapy device 50$^{IV}$ illustratively differs from the devices 50', 50" and 50"' in that the device 50$^{IV}$ includes one or more irradiation sources, one or more electrically conductive electrodes and one or more speakers, each as illustrated by example in the attached figures and described above. In this embodiment, the electrical circuit 80"' depicted in FIG. 18 includes circuitry described above for controlling, also as described above, the one or more electrically conductive electrodes, e.g., electrodes 302A-302D, circuitry described above for controlling, also as described above, the one or more irradiation sources, e.g., irradiation sources 58A-58D, and circuitry described above for controlling, also as described above, the one or more speakers 200.

Figure 19:
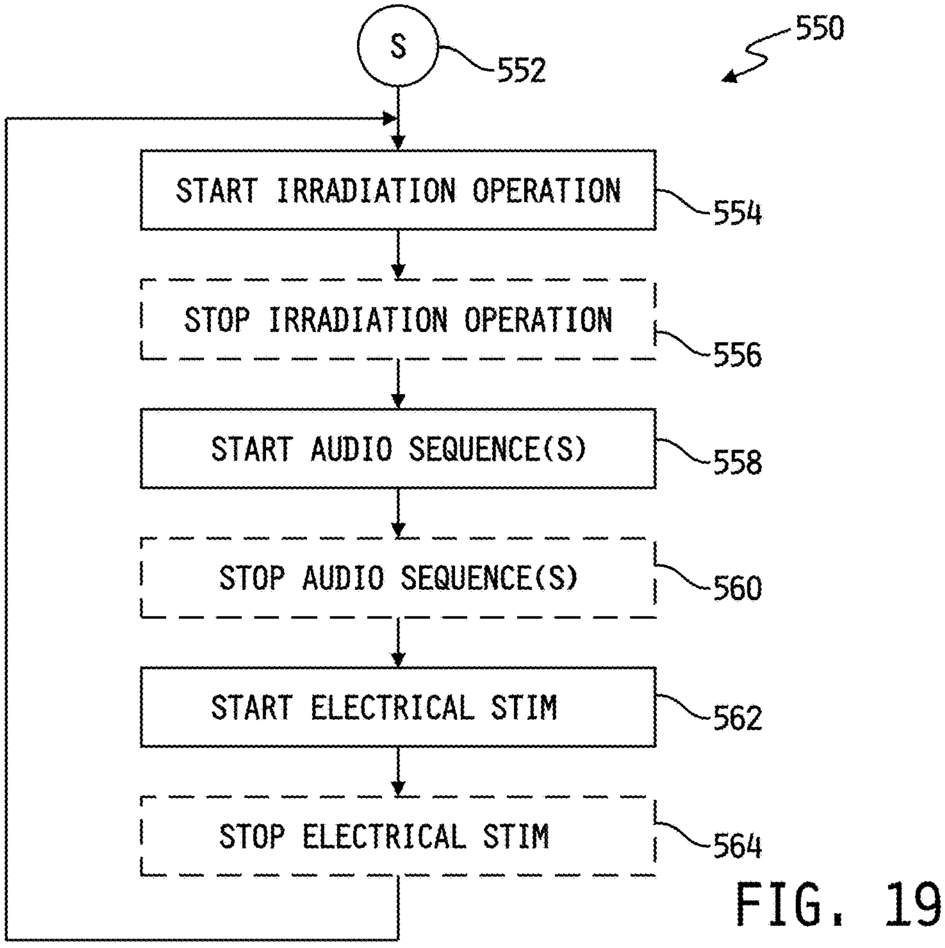
FIG. 19 is a flowchart illustrating an embodiment of a process for controlling operation of the external auditory canal therapy device of FIGS. 17 and 18.

Referring now to FIG. 19, a flowchart is shown of yet another embodiment of a process 550 for controlling one or more of the external auditory canal therapy devices 50$^{IV}$, and is thus yet another example of the therapy application 210 stored in the memory 108 of the mobile communication device 102' and executable by the processor 104. In alternate embodiments in which the mobile communication device 102' is not included, the electrical circuit 80"' may include one or more circuits, e.g., at least one processor and memory or other application specific circuits, configured to execute the process 550 illustrated in FIG. 19. In any case, the process 550 will be described as being executed by the processor 104, it being understood that the process 550 in alternate embodiments may be implemented and executed completely by the electrical circuit 80''' or by a combination of the processor 104 and the electrical circuit 80'''.

The process 550 begins at step 552, and thereafter at step 554 the processor 104 is operable to start an irradiation operation, i.e., to control the irradiation source(s) 58A-58D, to irradiate the external auditory meatus 18 via the inserted external auditory canal therapy device(s) $\mathbf{50}^{IV}$ as described above. In some embodiments of the process 550, step 556 may be included in which the processor 104 is operable to stop the irradiation sequence(s) by turning off or disabling irradiation by the irradiation source(s) 58A-58D prior to executing step 558 in which the processor 104 is operable to start an electrical stimulation operation, i.e., to control the electrically conductive electrode(s) 302A-302D, to electrically stimulate the external auditory meatus 18 via the inserted external auditory canal therapy device(s) $\mathbf{50}^{IV}$ as also described above. In such embodiments, the process 550 may also include step 560 in which the processor 104 is operable to stop the electrical stimulation sequence(s) by turning off or disabling electrical stimulation by the electrode(s) 302A-302D prior to executing step 562 in which the processor 104 is operable to start the audio sequence(s); i.e., to send or active one or more audio files so as to control the at least one speaker(s) 200 to produce corresponding acoustic waves as described above. In such embodiments, the process 550 may also include step 564 in which the processor 104 is operable to stop the audio sequence(s). In such embodiments, the electrical stimulation therapy, i.e., via the electrically conductive electrodes 302A-302D, the irradiation or photobiomodulation therapy, i.e., via the irradiation sources 58A-58D, and the audio therapy are alternated with one another. In some alternate embodiments, the various therapies may occur in any desired sequence(s) relative to one another.

In alternate embodiments of the process 550, steps 556, 560 and 564 may be omitted such that the irradiation or photobiomodulation therapy, the electrical stimulation therapy and the audio therapy may all be conducted simultaneously. In such embodiments, the photobiomodulation therapy, the electrical stimulation therapy or the audio therapy may be started before the others or they may all be started simultaneously. In some embodiments, the process 550 may loop so as to continually execute for some predetermined time period or until stopped by a user.

While this disclosure has been illustrated and described in detail in the foregoing drawings and description, the same is to be considered as illustrative and not restrictive in character, it being understood that only illustrative embodiments thereof have been shown and described and that all changes and modifications that come within the spirit of this disclosure are desired to be protected. For example, whereas the example photobiomodulation device 50 and 50' and the therapy devices 50'', 50''' and $\mathbf{50}^{IV}$ are illustrated as including an electrical circuit 80 (or 80', or 80'' or 80''') mounted to a circuit board 82 and operatively coupled to irradiation sources 58A-58D, electrically conductive electrodes 302A-302D and/or speaker(s) 200, wherein the electrical circuit 80, 80', 80'', 80''' includes circuit components for controlling operation of the irradiation sources 58A-58D, the electrodes 302A-302D and/or the speaker(s) 200, it will be understood that alternate embodiments are contemplated in which some or all of the electrical circuit 80, 80', 80'', 80''' is omitted. In one non-limiting embodiment, for example, in which the photobiomodulation device 50, the photobiomodulation and audio therapy device 50' and/or any of the external auditory canal therapy devices 50'', 50''', $\mathbf{50}^{IV}$ is/are configured to be hard-wire connected to a remote, mobile or stationary electronic control device, the electrical circuit 80, 80', 80'', 80''' may be omitted in its entirety, and the mobile or stationary electronic control device may be electrically coupled directly to the irradiation sources 58A-58D, the electrodes 302A-302D and/or the speaker(s) 200 via the hardwire connection such that the mobile or stationary device directly controls operation of the irradiation sources 58A-58D, the electrodes 302A-302D and/or the speaker(s) 200 in the same manner as described hereinabove. Alternatively or additionally, the electrical circuit 80, 80', 80'', 80''' in such embodiments may include one or more driver circuits electrically connected to the irradiation sources 58A-58D, the electrodes 302A-302D and/or speaker(s) 200 and electrically coupled directly to the mobile or stationary electronic control device via the hard-wire connection such that the mobile or stationary device controls operation of the irradiation sources 58A-58D, the electrodes 302A-302D and/or speaker(s) 200 via direct control of the one or more driver circuits. In either such example embodiment, the photobiomodulation device 50, the photobiomodulation and audio therapy device 50' and/or any of the external auditory canal therapy devices 50'', 50''', $\mathbf{50}^{IV}$ may include one or more sources of electrical power as illustrated in the figures and described above, or may instead receive electrical power from the mobile or stationary device via the hard-wire connection.

What is claimed is:

1. An external auditory canal therapy device, comprising:

a housing including a first portion configured to be inserted into an external auditory canal of a human ear and a second portion, a plurality of electrically conductive electrodes coupled to the housing such that, with the housing inserted into the external auditory canal, at least a portion of each of the plurality of electrically conductive electrodes non-percutaneously contacts at least a portion of dermis of the external auditory canal beneath which at least one of an arterial branch and a peripheral nerve branch of at least one cranial nerve is located, the plurality of electrically conductive electrodes disposed radially about the housing in spaced apart relation to one another around the housing and circumferentially aligned with one another, at least one irradiation source coupled to the housing such that, with the housing inserted into the external auditory canal, at least a portion of a radiation emitting surface of the at least one irradiation source faces at least another portion of dermis of the external auditory canal beneath which the at least one of the arterial branch and the peripheral nerve branch of the at least one cranial nerve is located, at least one speaker carried by the housing such that, with the housing inserted into the external auditory canal, acoustic waves exiting the at least one speaker pass through at least one opening defined through the housing and move through the external auditory canal toward a tympanic membrane of the human ear, and an electrical circuit carried by the housing, the electrical circuit including at least a first circuit component configured to control the plurality of electrically conductive electrodes to electrically stimulate the at least one of the arterial branch and the peripheral nerve branch of the at least one cranial nerve through the at least a portion of dermis of the external auditory canal, and at least a second circuit component configured to control the at least one irradiation source to irradiate the at least one of the arterial branch and the peripheral nerve branch of the at least one cranial nerve through the at least another portion of dermis of the external auditory canal, wherein the at least one irradiation source includes light sources arrayed circumferentially on the first portion of the housing, thereby positioning each of the light sources opposite to, and facing, the at least one of the arterial branch and peripheral nerve branch of the at least one cranial nerve.

2. The external auditory canal therapy device of claim 1, wherein the first portion of the housing is coupled to or integral with the second portion of the housing, the plurality of electrically conductive electrodes, the at least one irradiation source, and the at least one speaker coupled to the first portion of the housing, the second portion of the housing containing the electrical circuit.

3. An external auditory canal therapy system, comprising:

the external auditory canal therapy device of claim 1, wherein the electrical circuit of the external auditory canal therapy device includes a wireless communication circuit or a communication circuit for conducting hard-wire communications, and a mobile communication device including wireless communication circuitry configured to communicate wirelessly with the wireless communication circuit of the external auditory canal therapy device or including communication circuitry configured to communicate with the communication circuit of the external auditory canal therapy device via a hard-wire connection therebetween, the mobile communication device further comprising a processor programmed to control operation of the plurality of electrically conductive electrodes and operation of the at least one irradiation source and the at least one speaker of the external auditory canal therapy device by communicating operating instructions to the electrical circuit of the external auditory canal therapy device wirelessly or via hard-wire connection.

4. An external auditory canal therapy apparatus, comprising two of the external auditory canal therapy devices of claim 1, wherein the housing of one of the external auditory canal therapy devices is to be inserted into the external auditory canal of one ear of a human and the housing of the other of the external auditory canal therapy devices is to be inserted into the external auditory canal of an opposite ear of the human.

5. An external auditory canal therapy system, comprising:

the two external auditory canal therapy devices of claim 4, wherein the electrical circuit of each of the two external auditory canal therapy devices includes a wireless communication circuit or a communication circuit for conducting hard-wire communications, and a mobile communication device including wireless communication circuitry configured to communicate wirelessly with the wireless communication circuit of each of the two external auditory canal therapy devices or including communication circuitry configured to communicate with the communication circuit of each of the two external auditory canal therapy devices via a hard-wire connection therebetween, the mobile communication device further comprising a processor programmed to control operation of the plurality of electrically conductive electrodes, the at least one irradiation source, and the at least one speaker of each of the two external auditory canal therapy devices by communicating operating instructions to the electrical circuit of each of the two external auditory canal therapy devices wirelessly or via hard-wire connection.

6. An external auditory canal therapy device, comprising:

a housing including a first portion configured to be inserted into an external auditory canal of a human ear and a second portion, at least one irradiation source coupled to the housing such that, with the housing inserted into the external auditory canal, at least a portion of a radiation emitting surface thereof faces at least a portion of dermis of the external auditory canal beneath which at least one of an arterial branch and a peripheral nerve branch of at least one cranial nerve is located, wherein the at least the portion of the radiation emitting surface of the at least one irradiation source directs radiation radially outward ly from the housing, at least one electrically conductive electrode coupled to the housing such that, with the housing inserted into the external auditory canal, at least a portion of the at least one electrically conductive electrode non-percutaneously contacts at least another portion of dermis of the external auditory canal beneath which at least one of the arterial branch and the peripheral nerve branch of the at least one cranial nerve is located, and an electrical circuit carried by the housing and electrically connected to the at least one irradiation source and to the at least one electrically conductive electrode, the electrical circuit including at least a first circuit component configured to control the at least one irradiation source to irradiate the at least one of the arterial branch and the peripheral nerve branch of the at least one cranial nerve through the at least a portion of dermis of the external auditory canal, and at least a second circuit component configured to control the at least one electrically conductive electrode to electrically stimulate the at least one of the arterial branch and the peripheral nerve branch of the at least one cranial nerve through the at least another portion of dermis of the external auditory canal, wherein the at least one irradiation source includes light sources arrayed circumferentially on the first portion of the housing, thereby positioning each of the light sources opposite to, and facing, the at least one of the arterial branch and peripheral nerve branch of the at least one cranial nerve.

7. The external auditory canal therapy device of claim 6, further comprising means for controlling the at least the first circuit component and the at least the second circuit component to alternatingly cause the at least one irradiation source to produce radiation while the at least one electrically conductive electrode is not electrically stimulating the at least one of the arterial branch and the peripheral nerve branch of the at least one cranial nerve through the at least another portion of dermis of the external auditory canal, and to cause the at least one electrically conductive electrode to electrically stimulate the at least one of the arterial branch and the peripheral nerve branch of the at least one cranial nerve through the at least another portion of dermis of the external auditory canal while the at least one irradiation source is not producing radiation.

8. The external auditory canal therapy device of claim 6, further comprising means for controlling the at least the first circuit component and the at least the second circuit component to simultaneously cause the at least one irradiation source to produce radiation and the at least one electrically conductive electrode to electrically stimulate the at least one of the arterial branch and the peripheral nerve branch of the at least one cranial nerve through the at least another portion of dermis of the external auditory canal.

9. The external auditory canal therapy device of claim 6, wherein the at least one irradiation source is configured to produce electromagnetic radiation in at least one frequency or range of frequencies of visible light.

10. The external auditory canal therapy device of claim 6, wherein at least a portion of the housing has a curved outer periphery, and wherein the light sources and the at least one electrically conductive electrode include two or more light sources and two or more electrically conductive electrodes disposed radially about the curved outer periphery.

11. An external auditory canal therapy system, comprising:

the external auditory canal therapy device of claim 6, wherein the electrical circuit of the external auditory canal therapy device includes a wireless communication circuit or a communication circuit for conducting hard-wire communications, and a mobile communication device including wireless communication circuitry configured to communicate wirelessly with the wireless communication circuit of the external auditory canal therapy device or including communication circuitry configured to communicate with the communication circuit of the external auditory canal therapy device via a hard-wire connection therebetween, the mobile communication device further comprising a processor programmed to control operation of the at least one irradiation source and the at least one electrically conductive electrode of the external auditory canal therapy device by communicating operating instructions to the electrical circuit of the external auditory canal therapy device wirelessly or via hard-wire connection.

12. An external auditory canal therapy apparatus, comprising two of the external auditory canal therapy devices of claim 6, wherein the housing of one of the external auditory canal therapy devices is to be inserted into the external auditory canal of one ear of a human and the housing of the other of the external auditory canal therapy devices is to be inserted into the external auditory canal of an opposite ear of the human.

13. An external auditory canal therapy device, comprising:

a housing including a first portion configured to be inserted into an external auditory canal of a human ear and a second portion, the first portion of the housing defining at least one opening, a plurality of electrically conductive electrodes coupled to the housing such that, with the housing inserted into the external auditory canal, at least a portion of each of the plurality of electrically conductive electrodes non-percutaneously contacts at least a portion of dermis of the external auditory canal beneath which at least one of an arterial branch and a peripheral nerve branch of at least one cranial nerve is located, the plurality of electrically conductive electrodes disposed radially about the housing in spaced apart relation to one another around the housing and circumferentially aligned with one another, at least one speaker carried by the housing such that, with the housing inserted into the external auditory canal, acoustic waves exiting the at least one speaker pass through the at least one opening of the housing and move through the external auditory canal toward a tympanic membrane of the human ear, at least one irradiation source coupled to the housing such that, with the housing inserted into the external auditory canal, at least a portion of a radiation emitting surface of the at least one irradiation source faces at least another portion of dermis of the external auditory canal beneath which the at least one of the arterial branch and the peripheral nerve branch of the at least one cranial nerve is located, and an electrical circuit carried by the housing and electrically connected to the plurality of electrically conductive electrodes and to the at least one speaker, the electrical circuit including at least a first circuit component configured to control the plurality of electrically conductive electrodes to electrically stimulate the at least one of the arterial branch and the peripheral nerve branch of the at least one cranial nerve through the at least a portion of dermis of the external auditory canal, and at least a second circuit component configured to control the at least one speaker to produce acoustic waves, wherein the at least one irradiation source includes light sources arrayed circumferentially on the first portion of the housing, thereby positioning each of the light sources opposite to, and facing, the at least one of the arterial branch and peripheral nerve branch of the at least one cranial nerve.

14. The external auditory canal therapy device of claim 13, further comprising means for controlling the at least the first circuit component and the at least the second circuit component to alternatingly cause at least one of the plurality of electrically conductive electrodes to electrically stimulate the at least one of the arterial branch and the peripheral nerve branch of the at least one cranial nerve through the at least a portion of dermis of the external auditory canal while the at least one speaker is not producing acoustic waves, and to cause the at least one speaker to produce acoustic waves while the plurality of electrically conductive electrodes is not electrically stimulating the at least one of the arterial branch and the peripheral nerve branch of the at least one cranial nerve through the at least a portion of dermis of the external auditory canal.

15. The external auditory canal therapy device of claim 13, further comprising means for controlling the at least the first circuit component and the at least the second circuit component to simultaneously cause at least one of the plurality of electrically conductive electrodes to electrically stimulate the at least one of the arterial branch and the peripheral nerve branch of the at least one cranial nerve through the at least a portion of dermis of the external auditory canal and the at least one speaker to produce acoustic waves.

16. The external auditory canal therapy device of claim 13, wherein the acoustic waves include at least one of single frequency tone signals, multiple frequency tone signals, music signals, noise signals and beat signals.

17. An external auditory canal therapy system, comprising:

the external auditory canal therapy device of claim 13, wherein the electrical circuit of the external auditory canal therapy device includes a wireless communication circuit or a communication circuit for conducting hard-wire communications, and a mobile communication device including wireless communication circuitry configured to communicate wirelessly with the wireless communication circuit of the external auditory canal therapy device or including communication circuitry configured to communicate with the communication circuit of the external auditory canal therapy device via a hard-wire connection therebetween, the mobile communication device further comprising a processor programmed to control operation of the plurality of electrically conductive electrodes and the at least one speaker of the external auditory canal therapy device by communicating operating instructions to the electrical circuit of the external auditory canal therapy device wirelessly or via hard-wire connection.

18. The external auditory canal therapy system of claim 17, wherein the mobile communication device has stored therein, or is configured to access externally, one or more audio signal files, and wherein the operating instructions communicated to the external auditory canal therapy device by the mobile communication device include at least one of the one or more audio signal files, and wherein the at least a second circuit component is configured to supply audio signals from the at least one of the one or more audio signal files to the at least one speaker to cause the at least one speaker to produce the acoustic waves in the form of at least one of single frequency tone signals, multiple frequency tone signals, music signals, noise signals and beat signals.

19. An external auditory canal therapy apparatus, comprising two of the external auditory canal therapy devices of claim 13, wherein the housing of one of the external auditory canal therapy devices is to be inserted into the external auditory canal of one ear of a human and the housing of the other of the external auditory canal therapy devices is to be inserted into the external auditory canal of an opposite ear of the human.

20. An external auditory canal therapy device, comprising:

a housing including a first portion configured to be inserted into an external auditory canal of a human ear and a second portion, at least one irradiation source coupled to the housing such that, with the housing inserted into the external auditory canal, at least a portion of a radiation emitting surface thereof faces at least a portion of dermis of the external auditory canal beneath which at least one of an arterial branch and a peripheral nerve branch of at least one cranial nerve is located, wherein the at least the portion of the radiation emitting surface of the at least one irradiation source directs radiation radially outwardly from the housing, at least one electrically conductive electrode coupled to the housing such that, with the housing inserted into the external auditory canal, at least a portion of the at least one electrically conductive electrode non-percutaneously contacts at least another portion of dermis of the external auditory canal beneath which at least one of the arterial branch and the peripheral nerve branch of the at least one cranial nerve is located, at least one speaker carried by the housing such that, with the housing inserted into the external auditory canal, acoustic waves exiting the at least one speaker pass axially through at least one opening of the housing and move through the external auditory canal toward a tympanic membrane of the human ear, and an electrical circuit carried by the housing and electrically connected to the at least one irradiation source, the at least one electrically conductive electrode and the at least one speaker, the electrical circuit including at least a first circuit component configured to control the at least one irradiation source to irradiate the at least one of the arterial branch and the peripheral nerve branch of the at least one cranial nerve through the at least a portion of dermis of the external auditory canal, at least a second circuit component configured to control the at least one electrically conductive electrode to electrically stimulate the at least one of the arterial branch and the peripheral nerve branch of the at least one cranial nerve through the at least another portion of dermis of the external auditory canal, and at least a third circuit component configured to control the at least one speaker to produce acoustic waves, wherein the at least one irradiation source includes light sources arrayed circumferentially on the first portion of the housing, thereby positioning each of the light sources opposite to, and facing, the at least one of the arterial branch and peripheral nerve branch of the at least one cranial nerve.

* * * * *